United States Patent
Snell et al.

(10) Patent No.: US 10,556,225 B2
(45) Date of Patent: *Feb. 11, 2020

(54) METHODS OF REGENERATING AROMATIZATION CATALYSTS WITH A DECOKING STEP BETWEEN CHLORINE AND FLUORINE ADDITION

(71) Applicant: Chevron Phillips Chemical Company LP, The Woodlands, TX (US)

(72) Inventors: Ryan W. Snell, Kingwood, TX (US); Gabriela D. Alvez-Manoli, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/391,385

(22) Filed: Apr. 23, 2019

(65) Prior Publication Data

US 2019/0247833 A1 Aug. 15, 2019

Related U.S. Application Data

(63) Continuation of application No. 15/597,184, filed on May 17, 2015, now Pat. No. 10,307,740.

(51) Int. Cl.

| | |
|---|---|
| *B01J 38/46* | (2006.01) |
| *B01J 23/96* | (2006.01) |
| *B01J 23/42* | (2006.01) |
| *B01J 29/70* | (2006.01) |
| *B01J 35/00* | (2006.01) |
| *B01J 38/44* | (2006.01) |
| *B01J 38/66* | (2006.01) |
| *B01J 38/54* | (2006.01) |
| *B01J 38/02* | (2006.01) |
| *B01J 38/10* | (2006.01) |
| *C07C 5/41* | (2006.01) |
| *C10G 35/095* | (2006.01) |
| *C10G 35/04* | (2006.01) |
| *C10G 35/085* | (2006.01) |
| *B01J 38/04* | (2006.01) |
| *B01J 38/12* | (2006.01) |
| *B01J 38/42* | (2006.01) |
| *B01J 38/48* | (2006.01) |
| *B01J 29/62* | (2006.01) |
| *B01J 29/90* | (2006.01) |
| *C10G 35/06* | (2006.01) |

(52) U.S. Cl.
CPC .............. *B01J 23/96* (2013.01); *B01J 23/42* (2013.01); *B01J 29/62* (2013.01); *B01J 29/70* (2013.01); *B01J 29/90* (2013.01); *B01J 35/0006* (2013.01); *B01J 38/02* (2013.01); *B01J 38/04* (2013.01); *B01J 38/10* (2013.01); *B01J 38/12* (2013.01); *B01J 38/42* (2013.01); *B01J 38/44* (2013.01); *B01J 38/46* (2013.01); *B01J 38/48* (2013.01); *B01J 38/54* (2013.01); *B01J 38/66* (2013.01); *C07C 5/412* (2013.01); *C07C 5/415* (2013.01); *C07C 5/417* (2013.01); *C10G 35/04* (2013.01); *C10G 35/06* (2013.01); *C10G 35/085* (2013.01); *C10G 35/095* (2013.01); *C07C 2523/42* (2013.01); *C07C 2529/068* (2013.01); *C07C 2529/60* (2013.01); *C07C 2529/62* (2013.01); *C10G 2300/4037* (2013.01)

(58) Field of Classification Search
CPC ... B01J 38/04; B01J 38/12; B01J 38/42; B01J 38/44; B01J 38/46; B01J 38/48; C10G 35/04; C10G 35/06; C10G 35/095; C07C 2529/62; C07C 2529/068; C07C 5/417; C07C 5/415; C07C 5/412
USPC ...... 502/22, 32, 35, 36, 37, 38, 50; 208/135, 208/138, 139, 140
See application file for complete search history.

(56) References Cited

U.S. PATENT DOCUMENTS

| | | | |
|---|---|---|---|
| 2,906,702 | A | 9/1959 | Brennan et al. |
| 2,969,318 | A | 1/1961 | Woodall |
| 3,249,405 | A | 5/1966 | Waddill |
| 3,898,173 | A | 8/1975 | Hayes |
| 4,456,527 | A | 6/1984 | Buss et al. |
| 4,810,683 | A | 3/1989 | Cohn et al. |
| 4,937,215 | A | 6/1990 | Murakawa et al. |
| 5,155,074 | A | 10/1992 | Mohr |
| 5,196,631 | A | 3/1993 | Murakawa et al. |
| 5,260,238 | A | 11/1993 | Murakawa et al. |
| 5,389,235 | A | 2/1995 | Russ et al. |
| 5,401,365 | A | 3/1995 | Chen et al. |
| 5,401,386 | A | 3/1995 | Morrison et al. |
| 5,585,075 | A | 12/1996 | Takano et al. |
| 5,601,698 | A | 2/1997 | Innes |
| 6,121,180 | A | 9/2000 | Gevelinger |
| 6,190,539 | B1 | 2/2001 | Holtermann et al. |
| 6,207,042 | B1 | 3/2001 | Holtermann et al. |
| 6,406,614 | B1 | 6/2002 | Tiedtke et al. |
| 6,518,470 | B1 | 2/2003 | Fukunaga et al. |
| 6,812,180 | B2 | 11/2004 | Fukunaga |
| 7,153,801 | B2 | 12/2006 | Wu |
| 7,544,335 | B2 | 6/2009 | Scanlon et al. |
| 7,687,673 | B2 | 3/2010 | Ablin |
| 7,932,425 | B2 | 4/2011 | Blessing et al. |
| 8,664,144 | B2 | 3/2014 | Wu |
| 8,716,161 | B2 | 5/2014 | Wu |

(Continued)

*Primary Examiner* — Elizabeth D Wood
(74) *Attorney, Agent, or Firm* — Merchant & Gould P.C.

(57) ABSTRACT

Methods for regenerating a spent catalyst are disclosed. Such methods may employ a step of chlorinating the spent catalyst in the gas phase, followed by decoking the chlorinated spent catalyst, and then fluorinating the de-coked catalyst in a fluorine-containing solution of a fluorine-containing compound.

21 Claims, 4 Drawing Sheets

(56) References Cited

U.S. PATENT DOCUMENTS

| | | |
|---|---|---|
| 8,912,108 B2 | 12/2014 | Wu |
| 2002/0065443 A1 | 5/2002 | Williams et al. |
| 2010/0160147 A1 | 6/2010 | Wu |
| 2013/0231512 A1 | 9/2013 | Wu |
| 2014/0213839 A1 | 7/2014 | Wu |
| 2015/0073190 A1 | 3/2015 | Wu |
| 2016/0045904 A1 | 2/2016 | Wu |
| 2018/0333705 A1 | 11/2018 | Snell et al. |

METHODS OF REGENERATING AROMATIZATION CATALYSTS WITH A DECOKING STEP BETWEEN CHLORINE AND FLUORINE ADDITION

REFERENCE TO RELATED APPLICATION

This application is a continuation application of co-pending U.S. patent application Ser. No. 15/597,184, filed on May 17, 2017, now U.S. Pat. No. 10,307,740, the disclosure of which is incorporated herein by reference in its entirety.

FIELD OF THE INVENTION

The present disclosure concerns methods for the regeneration of spent catalysts, and more particularly relates to the regeneration of spent catalysts containing a transition metal, such as platinum, and a catalyst support.

BACKGROUND OF THE INVENTION

The catalytic conversion of non-aromatic hydrocarbons into aromatic compounds, often referred to as aromatization or reforming, is an important industrial process that may be used to produce benzene, toluene, xylenes, and the like. The aromatization or reforming process often is conducted in a reactor system that may contain one or more reactors containing transition metal based catalysts. These catalysts may provide increased selectivity to and/or increased yield of the desired aromatic compounds. However, under commercial reaction conditions, these catalysts slowly lose their activity, often simultaneously with a loss of selectivity to the desired aromatic compounds. Such catalysts are often referred to as "spent" catalysts once economic or operational thresholds are passed.

Because of their commercial importance and the expense incurred in producing fresh catalyst to replace the spent catalyst, there is an ongoing need for improved methods of restoring catalytic activity to spent catalysts. Accordingly, it is to this end that the present disclosure is generally directed.

SUMMARY OF THE INVENTION

Methods of regenerating spent catalysts comprising a transition metal and a catalyst support are disclosed and described herein. One such method for regenerating a spent catalyst may comprise (1) contacting the spent catalyst with a chlorine-containing stream comprising a chlorine-containing compound to produce a chlorinated spent catalyst, (2) contacting the chlorinated spent catalyst with a decoking gas stream comprising oxygen to produce a de-coked catalyst, and (3) contacting the de-coked catalyst with a fluorine-containing solution comprising a fluorine-containing compound to produce a fluorinated catalyst.

Another method for regenerating a spent catalyst consistent with this disclosure may comprise (a) contacting the spent catalyst with a pre-drying gas stream comprising an inert gas, (b) contacting the spent catalyst with a chlorine-containing stream comprising a chlorine-containing compound to produce a chlorinated spent catalyst, (c) contacting the chlorinated spent catalyst with a decoking gas stream comprising oxygen to produce a de-coked catalyst, (d) contacting the de-coked catalyst with a fluorine-containing solution comprising a fluorine-containing compound to produce a fluorinated catalyst, and (e) drying, calcining, or both drying and calcining the fluorinated catalyst.

Also disclosed herein are various processes for reforming hydrocarbons. An illustrative process may comprise (A) contacting a hydrocarbon feed with an aromatization catalyst comprising a transition metal and a catalyst support under reforming conditions in a reactor system to produce an aromatic product, (B) performing step (A) for a time period sufficient to form a spent catalyst, (C) contacting the spent catalyst with a chlorine-containing stream comprising a chlorine-containing compound to produce a chlorinated spent catalyst, (D) contacting the chlorinated spent catalyst with a decoking gas stream comprising oxygen to produce a de-coked catalyst, and (E) contacting the de-coked catalyst with a fluorine-containing solution comprising a fluorine-containing compound to produce a fluorinated catalyst.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

Figure 1:
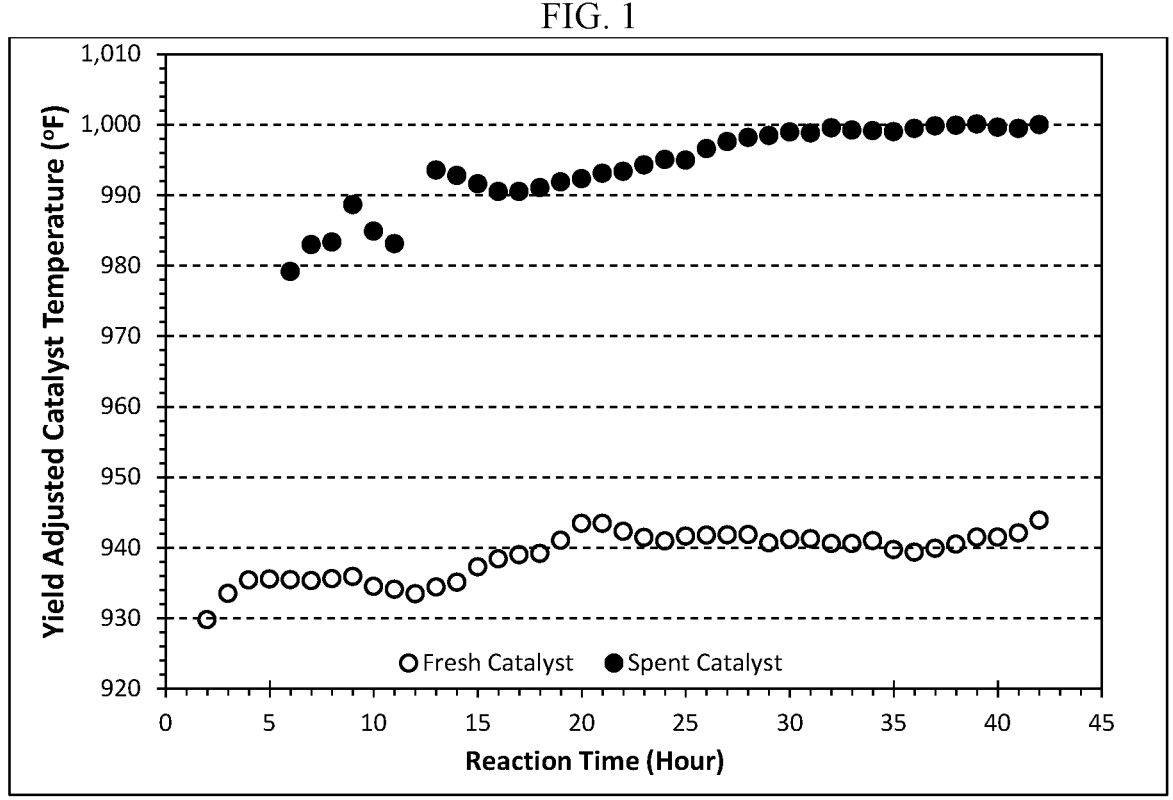
FIG. 1 presents a plot of the yield adjusted catalyst temperature versus reaction time for the fresh catalyst and the spent catalyst.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), may be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features may be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein may be combined to describe inventive designs, compositions, processes, or methods consistent with the present disclosure.

In this disclosure, while compositions and methods are often described in terms of "comprising" various components or steps, the compositions and methods may also "consist essentially of" or "consist of" the various components or steps, unless stated otherwise.

The terms "a," "an," and "the" are intended to include plural alternatives, e.g., at least one. For instance, the disclosure of "a transition metal" or "a chlorine-containing compound," is meant to encompass one, or mixtures or combinations of more than one, transition metal or chlorine-containing compound, unless otherwise specified.

A "spent" catalyst is used herein generally to describe a catalyst that has unacceptable performance in one or more of catalyst activity, hydrocarbon feed conversion, yield to a desired product(s), selectivity to a desired product(s), or an operating parameter, such as maximum operating temperature or pressure drop across a reactor, although the determination that a catalyst is "spent" is not limited only to these features. In some aspects, the "fresh" catalyst may have an activity X, the "spent" catalyst may have an activity Z, and a "regenerated" catalyst or a "reactivated" catalyst may have an activity Y, such that Z<Y<X. In certain aspects disclosed herein, the regenerated catalyst or reactivated catalyst may have substantially the same catalyst activity as that of the fresh catalyst. Such catalyst activity comparisons (and other reforming performance characteristics) are meant to use the same production run (batch) of catalyst, tested on the same equipment, and under the same test method and conditions. The "regenerated" catalyst encompasses catalysts regenerated using—at a minimum—the chlorination step, the decoking step, and the fluorination step described herein, while the "reactivated" catalyst is the "regenerated" catalyst that has been subjected to a reduction step (e.g., using hydrogen). As would be recognized by one of skill in the art in view of this disclosure, the "regenerated" catalyst is a generic term; it includes a catalyst that has been chlorinated, de-coked, and fluorinated, but also encompasses catalysts that have been subjected to one or more of any other catalyst regeneration steps disclosed herein, such as a chlorine purging step after chlorination, an oxygen purging step after the decoking step, a drying step and/or calcining step after fluorination, and so forth, as well as any combination thereof.

The amounts of any components or materials present on the catalysts described herein (e.g., fresh catalyst, spent catalyst, regenerated catalyst, or reactivated catalyst) are on a weight basis, such as wt. % or ppmw (ppm by weight), unless otherwise specified. These components or materials may include, for instance, the amount of carbon, the amount of fluorine, the amount of chlorine, the amount of platinum, and so forth. Moreover, these amounts are based on a "dry" catalyst, wherein the respective catalyst (e.g., fresh catalyst, spent catalyst, regenerated catalyst, or reactivated catalyst) has been dried to a solvent/water content of less than 10 wt. %.

Generally, groups of elements are indicated using the numbering scheme indicated in the version of the periodic table of elements published in Chemical and Engineering News, 63(5), 27, 1985. In some instances, a group of elements may be indicated using a common name assigned to the group; for example, alkali metals for Group 1 elements, alkaline earth metals for Group 2 elements, transition metals for Group 3-12 elements, noble metals for Group 8-10 elements, and halogens or halides for Group 17 elements.

For any particular compound or group disclosed herein, any name or structure (general or specific) presented is intended to encompass all conformational isomers, regioisomers, stereoisomers, and mixtures thereof that may arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes n-hexane, 2-methyl-pentane, 3-methyl-pentane, 2,2-dimethyl-butane, and 2,3-dimethyl-butane; and a general reference to a butyl group includes a n-butyl group, a sec-butyl group, an iso-butyl group, and a t-butyl group.

In one aspect, a chemical "group" may be defined or described according to how that group is formally derived from a reference or "parent" compound, for example, by the number of hydrogen atoms removed from the parent compound to generate the group, even if that group is not literally synthesized in such a manner. These groups may be utilized as substituents or coordinated or bonded to metal atoms. By way of example, an "alkyl group" formally may be derived by removing one hydrogen atom from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Various numerical ranges are disclosed herein. When a range of any type is disclosed or claimed herein, the intent is to disclose or claim individually each possible number that such a range could reasonably encompass, including end points of the range as well as any sub-ranges and combinations of sub-ranges encompassed therein, unless otherwise specified. As a representative example, the present application discloses that the methods provided herein may employ or produce a catalyst containing Cl and F at a molar ratio of Cl:F in a range from about 0.5:1 to about 4:1 in certain aspects. By a disclosure that the molar ratio of Cl:F may be in a range from about 0.5:1 to about 4:1, the intent is to recite that the molar ratio may be any molar ratio within the range and, for example, may be equal to about 0.5:1, about 0.6:1, about 0.7:1, about 0.8:1, about 0.9:1, about 1:1, about 2:1, about 3:1, or about 4:1. Additionally, the molar ratio of Cl:F may be within any range from about 0.5:1 to about 4:1 (for example, the molar ratio may be in a range from about 0.5:1 to about 2:1), and this also includes any combination of ranges between about 0.5:1 and about 4:1. Likewise, all other ranges disclosed herein should be interpreted in a manner similar to this example.

The term "about" means that amounts, sizes, formulations, parameters, and other quantities and characteristics are not and need not be exact, but may be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" may mean within 10% of the reported numerical value, preferably within 5% of the reported numerical value.

The term "substituted" when used to describe a group, for example, when referring to a substituted analog of a particular group, is intended to describe any non-hydrogen moiety that formally replaces a hydrogen atom in that group, and is intended to be non-limiting. A group or groups may also be referred to herein as "unsubstituted" or by equivalent terms such as "non-substituted," which refers to the original group in which a non-hydrogen moiety does not replace a hydrogen atom within that group. Unless otherwise specified, "substituted" is intended to be non-limiting and include inorganic substituents or organic substituents as understood by one of ordinary skill in the art.

As used herein, the term "hydrocarbon" refers to a compound containing only carbon and hydrogen atoms. Other identifiers may be utilized to indicate the presence of particular groups, if any, in the hydrocarbon (e.g., halogenated hydrocarbon indicates that the presence of one or more halogen atoms replacing an equivalent number of hydrogen atoms in the hydrocarbon).

An "aromatic" compound is a compound containing a cyclically conjugated double bond system that follows the Hickel (4n+2) rule and contains (4n+2) pi-electrons, where n is an integer from 1 to 5. Aromatic compounds include "arenes" (aromatic hydrocarbon compounds, e.g., benzene, toluene, and xylenes) and "heteroarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hickel rule (4n+2)). As disclosed herein, the term "substituted" may be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers may be utilized to indicate the presence of particular groups, if any, in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group may be linear or branched unless otherwise specified.

A "cycloalkane" is a saturated cyclic hydrocarbon, with or without side chains, for example, cyclobutane, cyclopentane, cyclohexane, methyl cyclopentane, and methyl cyclohexane. Other identifiers may be utilized to indicate the presence of particular groups, if any, in the cycloalkane (e.g., halogenated cycloalkane indicates that the presence of one or more halogen atoms replacing an equivalent number of hydrogen atoms in the cycloalkane).

The term "halogen" has its usual meaning. Examples of halogens include fluorine, chlorine, bromine, and iodine.

The term "contacting" is used herein to describe methods, processes, and compositions wherein the components are contacted or combined together in any order, in any manner, and for any length of time, unless otherwise specified. For example, the components may be contacted by blending or mixing. Further, unless otherwise specified, the contacting of any component may occur in the presence or absence of any other component of the methods, processes, and compositions described herein. Combining additional materials or components may be done by any suitable technique. Further, "contacting" two or more components may result in a solution, a slurry, a mixture, a reaction mixture, or a reaction product.

Molar selectivities are defined as:

$$\text{Benzene selectivity: } S_{Bz} = \frac{\dot{n}_{Bz,prod}}{\dot{n}_{conv\ C6,feed} - \dot{n}_{conv\ C6,prod}} \quad \text{Eq. 1}$$

$$\text{Toluene selectivity: } S_{Tol} = \frac{\dot{n}_{Tol,prod}}{\dot{n}_{conv\ C7,feed} - \dot{n}_{conv\ C7,prod}} \quad \text{Eq. 2}$$

$$\text{Benzene + Toluene selectivity: } S_{Bz+Tol} = \quad \text{Eq. 3}$$
$$\frac{\dot{n}_{Bz,prod} + \dot{n}_{Tol,prod}}{\dot{n}_{conv\ C6,C7,feed} - \dot{n}_{conv\ C6,C7,prod}}$$

$$\text{Aromatic selectivity: } S_{arom} = \frac{\dot{n}_{Bz,prod} + \dot{n}_{Tol,prod} + \dot{n}_{C8+\ arom,prod}}{\dot{n}_{conv\ C6-C8+,feed} - \dot{n}_{conv\ C6-C8+,prod}} \quad \text{Eq. 4}$$

Conversion is defined as the number of moles converted per mol of "convertible" hydrocarbons fed:

$$C6 \text{ conversion: } X_{C6} = \frac{\dot{n}_{conv\ C6,feed} - \dot{n}_{conv\ C6,prod}}{\dot{n}_{conv\ C6,feed}} \quad \text{Eq. 5}$$

$$C7 \text{ conversion: } X_{C7} = \frac{\dot{n}_{conv\ C7,feed} - \dot{n}_{conv\ C7,prod}}{\dot{n}_{conv\ C7,feed}} \quad \text{Eq. 6}$$

$$C6 + C7 \text{ conversion: } X_{C6+C7} = \quad \text{Eq. 7}$$
$$\frac{\dot{n}_{conv\ C6,feed} + \dot{n}_{conv\ C7,feed} - \dot{n}_{conv\ C6,prod} - \dot{n}_{conv\ C7,prod}}{\dot{n}_{conv\ C6,feed} + \dot{n}_{conv\ C7,feed}}$$

In these equations, n indicates a molar flow rate in a continuous reactor or the number of moles in a batch reactor.

As used herein, the term "convertible hydrocarbon," "convertible $C_6$ species," or "convertible $C_7$ species" refers to a hydrocarbon compound that is readily reacted to form aromatic hydrocarbons under aromatization process conditions. A "non-convertible hydrocarbon" is a highly-branched hydrocarbon that is not readily reacted to form aromatic hydrocarbons under aromatization process conditions. A "non-convertible hydrocarbon" may comprise highly-branched hydrocarbons having six or seven carbon atoms with an internal quaternary carbon, or hydrocarbons having six carbons atoms and two adjacent internal tertiary carbons, or mixtures thereof. A "convertible $C_6$ species" is a hydrocarbon containing six carbons without an internal quaternary carbon or two adjacent internal tertiary carbons, for example, n-hexane, 2-methyl-pentane, 3-methyl-pentane, cyclohexane, and methyl cyclopentane. A "convertible $C_7$ species" is a hydrocarbon containing seven carbons without an internal quaternary carbon, for example, n-heptane, 2-methyl-hexane, 3-methyl-hexane, 2,3-dimethyl-pentane, 2,4-dimethyl-pentane, methyl cyclohexane, and dimethyl cyclopentane. The highly branched hydrocarbons with six or seven carbon atoms and an internal quaternary carbon may comprise, for example, 2,2-dimethylbutane, 2,2-dimethylpentane, 3,3-dimethylpentane, and 2,2,3-trimethylbutane. The highly branched hydrocarbons with six carbon atoms and an adjacent internal tertiary carbon may comprise, for example, 2,3-dimethylbutane. The non-convertible highly branched hydrocarbons do not easily convert to aromatic products, and instead tend to convert to light hydrocarbons under aromatization process conditions.

Although any methods and materials similar or equivalent to those described herein may be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are methods for regenerating a spent catalyst. Related reforming processes also are disclosed. Beneficially, as compared to other methods of regenerating a spent catalyst, the methods described herein—e.g., a gas-phase chlorination step before a decoking or carbon burn step, and a liquid-phase fluorination step after the decoking or carbon burn step—result in a regenerated catalyst with minimal residual carbon, uniform chlorine and fluorine distribution, and unexpectedly improved catalyst activity and selectivity.

Methods for Regenerating Spent Catalysts

Various methods for regenerating spent catalysts comprising a transition metal and a catalyst support are disclosed and described. One such method for regenerating a spent catalyst may comprise (or consist essentially of, or consist of):

(1) contacting the spent catalyst with a chlorine-containing stream comprising a chlorine-containing compound to produce a chlorinated spent catalyst;

(2) contacting the chlorinated spent catalyst with a decoking gas stream comprising oxygen to produce a de-coked catalyst; and (3) contacting the de-coked catalyst with a fluorine-containing solution comprising a fluorine-containing compound to produce a fluorinated catalyst.

Generally, the features of any of the methods disclosed herein (e.g., the spent catalyst, the transition metal, the catalyst support, the fluorine-containing solution comprising the fluorine-containing compound, the chlorine-containing gas stream comprising the chlorine-containing compound, the conditions under which the fluorination step is conducted, the conditions under which the chlorination step is conducted, the decoking gas stream, and the conditions under which the decoking step is conducted, among others) are independently described herein, and these features may be combined in any combination to further describe the disclosed methods. Moreover, other process steps may be conducted before, during, and/or after any of the steps listed in the disclosed methods, unless stated otherwise. Additionally, reactivated or regenerated catalysts produced in accordance with any of the disclosed methods/processes are within the scope of this disclosure and are encompassed herein.

The steps of these methods that utilize a fluorine-containing solution comprising a fluorine-containing compound often may be referred to as fluorination steps, while the steps of these methods that utilize a chlorine-containing gas stream often may be referred to as chlorination steps. Any compositional attributes of the fluorine-containing solution (comprising the fluorine-containing compound) and the chlorine-containing gas stream (comprising the chlorine-containing compound) are meant to refer to the respective incoming fluorine-containing solution and incoming chlorine-containing gas stream, prior to contacting the catalyst, unless expressly stated otherwise. As one of skill in the art would readily recognize, the outgoing fluorine-containing solution effluent stream and the outgoing chlorine-containing effluent stream, after contacting the catalyst, may vary significantly in composition from the respective incoming fluorine-containing solution and the incoming chlorine-containing stream.

Referring now to step (1), the chlorine-containing compound in the chlorine-containing stream may be any suitable chlorine-containing compound or any chlorine-containing compound disclosed herein. For instance, illustrative chlorine-containing compounds may include, but are not limited to, hydrochloric acid, chlorine gas ($Cl_2$), carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethylammonium chloride, tetrapropylammonium chloride, tetrabutylammonium chloride, methyltriethylammonium chloride, and the like, or any combination thereof. Other suitable chlorine-containing compounds may include arenes and alkyl-substituted arenes (e.g., benzene, toluene, and xylenes) where at least one hydrogen atom is replaced with a Cl atom.

In some aspects, the chlorine-containing compound may comprise (or consist essentially of, or consist of) hydrochloric acid; alternatively, chlorine gas ($Cl_2$); alternatively, carbon tetrachloride; alternatively, tetrachloroethylene; alternatively, chlorobenzene; alternatively, methyl chloride; alternatively, methylene chloride; alternatively, chloroform; alternatively, allyl chloride; alternatively, trichloroethylene; alternatively, a chloramine; alternatively, a chlorine oxide; alternatively, a chlorine acid; alternatively, chlorine dioxide; alternatively, dichlorine monoxide; alternatively, dichlorine heptoxide; alternatively, chloric acid; alternatively, perchloric acid; alternatively, ammonium chloride; alternatively, tetramethylammonium chloride; alternatively, tetraethylammonium chloride; alternatively, tetrapropylammonium chloride; alternatively, tetrabutylammonium chloride; or alternatively, methyltriethylammonium chloride.

In other aspects, the chlorine-containing compound may comprise (or consist essentially of, or consist of) chlorine gas ($Cl_2$). In addition to chlorine, the chlorine-containing stream may further comprise an inert gas, such as helium, neon, argon, or nitrogen, or combinations of two or more of these materials. In certain aspects, the chlorine-containing stream may comprise (or consist essentially of, or consist of) a chlorine-containing compound and an inert gas, and the inert gas may be or may comprise nitrogen. In a further aspect, the chlorine-containing stream may comprise (or consist essentially of, or consist of) chlorine gas ($Cl_2$) and nitrogen.

While not being limited thereto, the amount of chlorine (Cl) in the chlorine-containing stream often may be less than about 10 vol. %. For instance, the amount of the chlorine-containing compound in the chlorine-containing stream may provide (or result in) an amount of Cl in the chlorine-containing stream of less than about 7 vol. %; alternatively, less than about 5 vol. %; alternatively, less than about 4 vol. %; or alternatively, less than about 3 vol. %. In some aspects, the amount of the chlorine-containing compound in the chlorine-containing stream may provide (or result in) an amount of Cl in the chlorine-containing stream in a range of from about 0.05 to about 7 vol. %, from about 0.05 to about 5 vol. %, from about 0.05 to about 3 vol. %, from about 0.05 to about 2 vol. %, from about 0.1 to about 10 vol. %, from about 0.1 to about 5 vol. %, from about 0.5 to about 7 vol. %, from about 0.5 to about 5 vol. %, from about 0.5 to about 3 vol. %, from about 1 to about 10 vol. %, from about 1 to about 5 vol. %, or from about 1 to about 3 vol. %, and the like.

The chlorine-containing stream may be substantially free of oxygen-containing compounds (e.g., oxygen ($O_2$) and water ($H_2O$)), i.e., may contain less than 100 ppmw (ppm by weight) of oxygen-containing compounds. Therefore, it is contemplated that the amount of oxygen-containing compounds in the chlorine-containing stream may be less than 50 ppmw, less than 25 ppmw, less than 10 ppmw, less than 5 ppmw, or less than 3 ppmw, in certain aspects. In other aspects, the amount of oxygen-containing compounds in the chlorine-containing stream may be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no oxygen added during the chlorination step of the method of regenerating a spent catalyst. Moreover, although not required, the chlorine-containing stream may be substantially free of fluorine-containing compounds, i.e., may contain less than 100 ppmw (ppm by weight) of fluorine-containing compounds. As above, it is contemplated that the amount of fluorine-containing compounds in the chlorine-containing stream may be, for instance, less than 50 ppmw, less than 10 ppmw, in a range from about 0.1 to 100 ppmw, in a range from about 0.1 to about 50 ppmw, or in a range from about 0.1 to about 10 ppmw, and the like.

The chlorination step may be conducted at a variety of temperatures and time periods. For instance, the chlorination step may be conducted at a chlorination temperature in a range from about 20° C. to about 500° C.; alternatively, from about 20° C. to about 300° C.; alternatively, from about 25° C. to about 300° C.; alternatively, from about 30° C. to about 250° C.; alternatively, from about 30° C. to about 150° C.; alternatively, from about 35° C. to about 300° C.; alternatively, from about 35° C. to about 200° C.; alternatively, from about 50° C. to about 250° C.; alternatively, from about 50° C. to about 200° C.; alternatively, from about 100° C. to about 300° C.; alternatively, from about 100° C. to about 250° C.; or alternatively, from about 150° C. to about 275° C. In these and other aspects, these temperature ranges also are meant to encompass circumstances where the chlorination step is conducted at a series of different temperatures, instead of at a single fixed temperature, falling within the respective ranges.

The duration of the chlorination step is not limited to any particular period of time. Hence, the chlorination step may be conducted, for example, in a time period ranging from as little as 30-45 minutes to as long as 12-24 hours, 36-48 hours, or more. The appropriate chlorination time may depend upon, for example, the chlorination temperature and the amount of chlorine (Cl) in the chlorine-containing stream, among other variables. Generally, however, the chlorination step may be conducted in a time period that may be in a range from about 45 minutes to about 48 hours, such as, for example, from about 1 hour to about 48 hours, from about 45 minutes to about 24 hours, from about 45 minutes to about 18 hours, from about 1 hour to about 12 hours, from about 2 hours to about 12 hours, from about 4 hours to about 10 hours, or from about 2 hours to about 8 hours.

In other aspects, the chlorination step may be conducted for a time period determined by monitoring for the presence of chlorine or chlorine-containing compounds in the outgoing chlorine-containing effluent stream, after contacting the catalyst. Hence, the chlorination step may be conducted for a time period sufficient for the presence of chlorine-containing compounds to in the chlorine-containing effluent stream, after contacting the catalyst, to be more than 0.5 ppmv, for example, more than 1 ppmv, or more than 10 ppmv.

Step (2) of the method for regenerating a spent catalyst often may be referred to as the carbon burn step, or decoking step, and in this step, a chlorinated spent catalyst may be contacted with a decoking gas stream comprising oxygen to produce a de-coked catalyst. In addition to oxygen, the decoking gas stream may comprise an inert gas, i.e., the decoking gas stream may comprise (or consist essentially of, or consist of) oxygen and an inert gas. Typical inert gasses useful in the carbon burn step may encompass helium, neon, argon, nitrogen, and the like, and this includes combinations of two or more of these materials. In certain aspects, the decoking gas stream may comprise (or consist essentially of, or consist of) oxygen and nitrogen; alternatively, air and nitrogen; or alternatively, air.

Since the decoking gas stream may comprise air, the decoking gas stream may comprise about 20-21 mole % oxygen. More often, however, the amount of oxygen in the decoking gas may be less than about 10 mole %. For example, in some aspects, the decoking gas stream may comprise less than about 8 mole %, less than about 5 mole %, or less than about 3 mole % oxygen. Accordingly, suitable ranges for the mole % of oxygen in the decoking gas stream may include, but are not limited to, the following ranges: from about 0.1 to about 25 mole %, from about 0.1 to about 20 mole %, from about 0.1 to about 10 mole %, from about 0.2 to about 10 mole %, from about 0.2 to about 5 mole %, from about 0.3 to about 5 mole %, from about 0.5 to about 5 mole %, from about 0.5 to about 4 mole %, from about 0.5 to about 2 mole %, or from about 1 to about 3 mole %, and the like.

In an aspect, the decoking gas stream may be substantially halogen-free, i.e., substantially free of halogen-containing compounds. In this context, "substantially halogen-free" means less than 100 ppmw (ppm by weight) of halogen-containing compounds, such as chlorine-containing compounds, in the decoking gas stream. Therefore, it is contemplated that the amount of halogen-containing compounds in the decoking gas stream may be less than 50 ppmw, less than 40 ppmw, less than 25 ppmw, less than 10 ppmw, less than 5 ppmw, or less than 3 ppmw, in certain aspects. In other aspects, the amount of halogen-containing compounds in the decoking gas stream may be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no halogens or halogen-containing compounds, such as chlorine, added during the carbon burn step of the method of regenerating a spent catalyst.

In another aspect, the decoking gas stream may comprise water at an amount of greater than about 500 ppmw (ppm by weight), greater than about 1000 ppmw, or greater than about 5000 ppmw, if desired. Alternatively, the decoking gas stream may be substantially free of water, and in this regard, "substantially free" means less than 100 ppmw (ppm by weight) of water in the decoking gas stream. Therefore, it is contemplated that the amount of water in the decoking gas stream may be less than 50 ppmw, less than 25 ppmw, less than 10 ppmw, less than 5 ppmw, or less than 3 ppmw, in certain aspects. In other aspects, the amount of water in the decoking gas stream may be in range from about 0.1 to 100 ppmw, from about 0.5 to 100 ppmw, from about 1 to 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no water added during the carbon burn step of the method of regenerating a spent catalyst.

Similar to that described above for the chlorine-containing stream, any compositional attributes of the decoking gas stream are meant to refer to the incoming decoking gas stream, prior to contacting the chlorinated spent catalyst, unless expressly stated otherwise. As one of skill in the art would readily recognize, the outgoing decoking gas effluent stream, after contacting the chlorinated spent catalyst, may vary significantly in composition from the incoming decoking gas stream. For instance, chlorine adsorbed during the chlorination step may elute, in some circumstances, from the catalyst during the carbon burn step. Moreover, water may be produced during the carbon burn step, and thus, water may be detected in the outgoing decoking effluent stream.

The carbon burn step may be conducted at a variety of temperatures and time periods. For instance, the carbon burn step may be conducted at a peak decoking temperature in a range from about 150° C. to about 600° C.; alternatively, from about 200° C. to about 500° C.; alternatively, from about 300° C. to about 600° C.; alternatively, from about 300° C. to about 550° C.; alternatively, from about 300° C. to about 500° C.; alternatively, from about 320° C. to about 480° C.; alternatively, from about 340° C. to about 460° C.; or alternatively, from about 350° C. to about 450° C. In these and other aspects, these temperature ranges also are meant to encompass circumstances where the carbon burn step is conducted at a series of different temperatures (e.g., an initial decoking temperature, a peak decoking temperature), instead of at a single fixed temperature, falling within the respective ranges. For instance, and not limited thereto, the carbon burn step may be started at an initial decoking temperature which is the same as the chlorination temperature. Thus, for example, the carbon burn step may commence at an initial decoking temperature in a range from about 20° C. to about 250° C., from about 50° C. to about 200° C., or from about 150° C. to about 260° C. Subsequently, the temperature of the carbon burn step may be increased to a peak decoking temperature, for example, in a range from about 300° C. to about 600° C., or from about 350° C. to about 450° C.

The duration of the carbon burn step is not limited to any particular period of time. Hence, the carbon burn step may be conducted, for example, in a time period ranging from as little as 30-45 minutes to as long as 48-72 hours, or more. The appropriate decoking time may depend upon, for example, the initial/peak decoking temperature and the amount of oxygen in the decoking gas stream, among other variables. Generally, however, the carbon burn step may be conducted in a time period that may be in a range from about 45 minutes to about 72 hours, such as, for example, from about 1 hour to about 72 hours, from about 24 hours to about 72 hours, from about 12 hours to about 60 hours, from about 12 hours to about 48 hours, or from about 1 hour to about 6 hours.

Alternatively, the carbon burn step may be conducted for a time period sufficient to reduce the wt. % of carbon on the chlorinated spent catalyst to less than about 1 wt. % (a de-coked catalyst). In some aspects, the carbon burn step may be conducted for a time period sufficient to reduce the wt. % of carbon on the chlorinated spent catalyst to less than about 0.75 wt. %, less than about 0.5 wt. %, or less than about 0.2 wt. %. In other aspects, the carbon burn step may be conducted for a time period determined by monitoring the $CO_2$ level in the outgoing decoking effluent stream, after contacting the catalyst. Hence, the carbon burn step may be conducted for a time period sufficient to reduce the amount of $CO_2$ in the outgoing decoking effluent stream, after contacting the catalyst, to less than about 100 ppmv, for example, less than about 50 ppmv, or less than about 20 ppmv.

Alternatively, the carbon burn step may be conducted for a time period sufficient to result in a de-coked catalyst having an activity that is from about 50% to about 100% of the activity of the fresh catalyst, for example, from about 60% to about 100%, or from about 75% to about 100%. In this regard, the activity of the de-coked catalyst is based on returning to within about 50%-100% of the fresh catalyst activity of the same production run of catalyst, tested on the same equipment and under the same method and conditions.

In step (3) of the method for regenerating a spent catalyst, the de-coked catalyst may be contacted with a fluorine-containing solution comprising a fluorine-containing compound to produce a fluorinated catalyst. In one aspect, the fluorine-containing solution may comprise (or consist essentially of, or consist of) the fluorine-containing compound and water, while in another aspect, the fluorine-containing solution may comprise (or consist essentially of, or consist of) the fluorine-containing compound and a hydrocarbon solvent. When a hydrocarbon solvent is used, non-polar aliphatic hydrocarbons such as cyclohexane, isobutane, n-butane, n-pentane, isopentane, neopentane, n-hexane, n-heptane, and the like, or combinations thereof, may be used. Additionally or alternatively, an aromatic hydrocarbon may be used, non-limiting examples of which may include toluene, benzene, xylenes, and the like, or combinations thereof.

The fluorination step may be conducted using any suitable technique and equipment, for example, to result in uniform distribution of the fluorine. For instance, the de-coked catalyst may be placed into a vessel or tank, and then filled with enough of the fluorine-containing solution (comprising the fluorine-containing compound) to exceed the level of the catalyst in the vessel or tank. Optionally, agitation may be provided in the vessel and tank to increase the contact between the catalyst and the fluorine-containing compound within the fluorine-containing solution. Alternatively, the de-coked catalyst may be placed in a fixed or packed bed arrangement, and the fluorine-containing solution comprising the fluorine-containing compound may be contacted with the catalyst by flowing the fluorine-containing solution through the bed of the catalyst. Alternatively, the de-coked catalyst may be impregnated to incipient wetness with the fluorine-containing solution (comprising the fluorine-containing compound), wherein the pore filling or "incipient wetness" impregnation technique used is a method in which an amount of the fluorine-containing solution equal to the pore volume of the de-coked catalyst is mixed with the de-coked catalyst until the pores are filled. In the incipient wetness impregnation technique, the de-coked catalyst may be placed into a rotating drum, and the fluorine-containing solution (comprising the fluorine-containing compound) may be poured, sprayed or otherwise uniformly added onto the catalyst. The end point of this method may vary somewhat from laboratory to laboratory, so that an impregnated catalyst could have a free-flowing dry appearance to the first appearances of clumping. However, typically there would not be any free-flowing liquid present when the incipient wetness method is employed. As would be recognized by those of skill in the art, other suitable techniques and equipment may be employed for the fluorination step, and such techniques and equipment are encompassed herein.

Suitable fluorine-containing compounds may include, but are not limited to, hydrofluoric acid, 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethylammonium fluoride, tetrapropylammonium fluoride, tetrabutylammonium fluoride, methyltriethylammonium fluoride, and the like, or any combination thereof. Other suitable fluorine-containing compounds may include arenes and alkyl-substituted arenes (e.g., benzene, toluene, and xylenes) where at least one hydrogen atom is replaced with a F atom.

In another aspect, the fluorine-containing compound may comprise (or consist essentially of, or consist of) hydrofluoric acid, ammonium fluoride, tetramethylammonium fluoride, or a combination thereof; alternatively, hydrofluoric acid; alternatively, 2,2,2-trifluoroethanol; alternatively, tetrafluoroethylene; alternatively, carbon tetrafluoride; alternatively, carbon trifluoride; alternatively, fluoromethane; alternatively, heptafluoropropane; alternatively, decafluorobutane; alternatively, hexafluoroisopropanol; alternatively, tetrafluoropropanol; alternatively, pentafluoropropanol; alternatively, hexafluorophenylpropanol; alternatively, perfluorobutyl alcohol; alternatively, hexafluor-2-propanol; alternatively, pentafluoro-1-propanol; alternatively, tetrafluoro-1-propanol; alternatively, 1,1,1,3,3,3-hexafluoro-2-propanol; alternatively, 2,2,3,3,3-pentafluoro-1-propanol; alternatively, ammonium fluoride; alternatively, tetramethylammonium fluoride; alternatively, tetraethylammonium fluoride; alternatively, tetrapropylammonium fluoride; alternatively, tetrabutylammonium fluoride; or alternatively, methyltriethylammonium fluoride.

In yet another aspect, the fluorine-containing solution may comprise (or consist essentially of, or consist of) water and a fluorine-containing compound, and the fluorine-containing compound may comprise ammonium fluoride; alternatively, tetramethylammonium fluoride; alternatively, tetraethylammonium fluoride; alternatively, tetrapropylammonium fluoride; alternatively, tetrabutylammonium fluoride; or alternatively, methyltriethylammonium fluoride, or a combination thereof. In still another aspect, the fluorine-containing solution may comprise (or consist essentially of, or consist of) water and hydrofluoric acid; alternatively, water and ammonium fluoride; or alternatively, water and tetramethylammonium fluoride.

While not being limited thereto, the amount of fluorine (F) in the fluorine-containing solution often may be less than about 15 wt. %. For instance, the amount of the fluorine-containing compound in the fluorine-containing solution may provide (or result in) an amount of F in the fluorine-containing solution of less than about 10 wt. %; alternatively, less than about 8 wt. %; alternatively, less than about 5 wt. %; or alternatively, less than about 3 wt. %. In some aspects, the amount of the fluorine-containing compound in the fluorine-containing solution may provide (or result in) an amount of F in the fluorine-containing solution in a range of from about 0.01 to about 10 wt. %, from about 0.1 to about 10 wt. %, from about 0.5 to about 10 wt. %, from about 1 to about 10 wt. %, from about 0.01 to about 8 wt. %, from about 0.1 to about 8 wt. %, from about 1 to about 8 wt. %, from about 0.01 to about 5 wt. %, from about 0.1 to about 5 wt. %, from about 0.5 to about 5 wt. %, or from about 1 to about 5 wt. %, and the like.

Moreover, although not required, the fluorine-containing solution comprising the fluorine-containing compound may be substantially free of chlorine-containing compounds, i.e., may contain less than 100 ppmw (ppm by weight) of chlorine-containing compounds. It is contemplated that the amount of chlorine-containing compounds in the fluorine-containing solution may be, for instance, less than 50 ppmw, less than 10 ppmw, in a range from about 0.1 to 100 ppmw, in a range from about 0.1 to about 50 ppmw, or in a range from about 0.1 to about 10 ppmw, and the like.

The fluorination step may be conducted at a variety of temperatures and time periods. For instance, the fluorination step may be conducted at a fluorination temperature in a range from about 20° C. to about 95° C.; alternatively, from about 20° C. to about 80° C.; alternatively, from about 20° C. to about 50° C.; alternatively, from about 25° C. to about 95° C.; alternatively, from about 25° C. to about 80° C.; alternatively, from about 25° C. to about 50° C.; alternatively, from about 20° C. to about 35° C.; alternatively, from about 30° C. to about 80° C.; alternatively, from about 30° C. to about 50° C.; alternatively, from about 35° C. to about 95° C.; or alternatively, from about 35° C. to about 50° C. In these and other aspects, these temperature ranges also are meant to encompass circumstances where the fluorination step is conducted at a series of different temperatures, instead of at a single fixed temperature, falling within the respective ranges.

The duration of the fluorination step is not limited to any particular period of time. Hence, the fluorination step may be conducted, for example, in a time period ranging from as little as 1-5 minutes to as long as 12-24 hours, 36-48 hours, or more. The appropriate fluorination time may depend upon, for example, the fluorination temperature and the amount of fluorine in the fluorine-containing solution, among other variables. Generally, however, the fluorination step may be conducted in a time period that may be in a range from about 1 minute to about 48 hours, such as, for example, from about 15 minutes to about 48 hours, from about 10 minutes to about 24 hours, from about 30 minutes to about 18 hours, from about 30 minutes to about 12 hours, from about 30 minutes to about 6 hours, from about 1 hour to about 10 hours, or from about 2 hours to about 8 hours.

In some aspects, it may be desirable to age the de-coked catalyst impregnated with the fluorine-containing solution. The aging step may be performed at temperatures from about 20° C. to about 100° C., at pressures from about ambient to about 500 psig, for periods of time from about 1 minute to about 10 days, and under conditions where the impregnated solid is stationary or moving. Generally, however, the aging step may be conducted for a time period that may be in a range from about 1 minute to about 48 hours, such as, for example, from about 5 minutes to about 12 hours, from about 10 minutes to about 6 hours, from about 30 minutes to about 2 hours, or from about 30 minutes to about 1 hour.

In various aspects contemplated herein, the methods of regenerating a spent catalyst may further include one or more optional steps performed prior to the chlorination step. For example, a method of regenerating a spent catalyst may further comprise a partial decoking step prior to the chlorination step, and/or may further comprise a pre-drying step prior to the chlorination step. These optional pre-chlorination steps are discussed in greater detail herein below. In one aspect, at least one of these optional steps may be performed in a method of regenerating a spent catalyst, while in another aspect, both of these optional steps may be performed. The pre-chlorination steps may be performed in any order, however, in a particular aspect, the partial decoking step may be performed first, followed by the pre-drying step.

In an aspect, a method of regenerating a spent catalyst (e.g., comprising a transition metal and a catalyst support) comprising a chlorination step, followed by a carbon burn step, and then by a fluorination step, may further comprise a partial decoking step prior to the chlorination step. This partial decoking step generally may comprise contacting the spent catalyst with a partial decoking gas stream comprising oxygen.

The composition of the partial decoking gas stream may encompass the same potential attributes as that described above for the decoking gas stream employed in the carbon burn step. Thus, in addition to oxygen, the partial decoking gas stream may comprise an inert gas, such as helium, neon, argon, nitrogen, or combinations of two or more of these materials. In an aspect, the partial decoking gas stream may comprise (or consist essentially of, or consist of) oxygen and nitrogen; alternatively, air and nitrogen; or alternatively, air. In another aspect, the partial decoking gas stream often may comprise, for example, from about 0.1 to about 25 mole % oxygen, from about 0.1 to about 20 mole % oxygen, from about 0.2 to about 10 mole % oxygen, from about 0.2 to about 5 mole % oxygen, from about 0.3 to about 5 mole % oxygen, from about 0.5 to about 5 mole % oxygen, from about 0.5 to about 4 mole % oxygen, from about 0.5 to about 3 mole % oxygen, or from about 1 to about 3 mole % oxygen, and the like. In yet another aspect, the partial decoking gas stream may be substantially halogen-free or substantially free of halogen-containing compounds, i.e., having less than 100 ppmw (ppm by weight) of halogen-containing compounds in the partial decoking gas stream, such as, for example, less than 50 ppmw, less than 25 ppmw, less than 10 ppmw, less than 5 ppmw, or less than 3 ppmw, of halogen-containing compounds in the partial decoking gas stream. In still another aspect, the partial decoking gas stream may be substantially free of water, i.e., having less than 100 ppmw of water in the partial decoking gas stream, such as, for example, less than 50 ppmw, less than 25 ppmw, less than 10 ppmw, less than 5 ppmw, or less than 3 ppmw, of water in the partial decoking gas stream.

The partial decoking step differs from the carbon burn step in that it may be conducted at a much lower temperature. Generally, the partial decoking step may be conducted at a partial decoking temperature in a range from about 125° C. to about 450° C.; alternatively, from about 125° C. to about 350° C.; alternatively, from about 150° C. to about 250° C.; alternatively, from about 175° C. to about 250° C.; alternatively, from about 150° C. to about 225° C.; or alternatively, from about 175° C. to about 225° C. In these and other aspects, these temperature ranges also are meant to encompass circumstances where the partial decoking step is conducted at a series of different temperatures, instead of at a single fixed temperature, falling within the respective ranges.

The duration of the partial decoking step is not limited to any particular period of time. Typically, the partial decoking step may be conducted in a time period ranging from as little as 30-45 minutes to as long as 48 hours (or more), but more typically, the partial decoking step may be conducted in a time period that may be in a range from about 1 hour to about 36 hours, such as, for example, from about 2 hours to about 36 hours, from about 1 hour to about 24 hours, from about 1 hour to about 18 hours, or from about 2 hours to about 24 hours.

Alternatively, the partial decoking step may be conducted for a time period sufficient to reduce the wt. % of carbon on the spent catalyst to less than 3 wt. %, or less than 2 wt. %. Alternatively, the partial decoking step may be conducted for a time period sufficient to reduce the wt. % of carbon on the spent catalyst to within a range from about 0.1 to about 10 wt. %, such as, for example, from about 0.1 to about 6 wt. %, from about 1 to about 5 wt. %, from about 0.5 to about 4 wt. %, from about 1 to about 3 wt. %, or from about 0.5 to about 2 wt. % carbon. While not wishing to be bound by theory, it is believed that operational health and safety benefits may be achieved by removing hydrocarbons, particularly aromatic hydrocarbons, and light oligomers prior to regenerating the spent catalyst or opening an aromatization reactor.

In an aspect, a method of regenerating a spent catalyst (e.g., comprising a transition metal and a catalyst support) comprising a chlorination step, followed by a carbon burn step, and then by a fluorination step, may further comprise a pre-drying step prior to the chlorination step. This pre-drying step generally may comprise contacting the spent catalyst with a pre-drying gas stream comprising (or consisting essentially of, or consisting of) an inert gas. The inert gas may be helium, neon, argon, or nitrogen, or mixtures thereof; alternatively, helium; alternatively, neon; alternatively, argon; or alternatively, nitrogen. Additionally, in some aspects, the pre-drying gas stream may be substantially free of oxygen-containing compounds (e.g., oxygen or water), as discussed above in relation to the chlorination step. Hence, the pre-drying step may be conducted in the presence of less than 100 ppmw of oxygen-containing compounds, or less than 50 ppmw, or less than 25 ppmw, or less than 10 ppmw, or less than 5 ppmw, or less than 3 ppmw.

The pre-drying step may be performed at a pre-drying temperature that generally may encompass the same temperature range as the chlorination temperature used in the chlorination step. Accordingly, the pre-drying temperature may be in a range from about 20° C. to about 500° C.; alternatively, from about 20° C. to about 400° C.; alternatively, from about 25° C. to about 300° C.; alternatively, from about 30° C. to about 250° C.; alternatively, from about 30° C. to about 150° C.; alternatively, from about 35° C. to about 300° C.; alternatively, from about 35° C. to about 200° C.; alternatively, from about 50° C. to about 250° C.; alternatively, from about 50° C. to about 200° C.; alternatively, from about 100° C. to about 500° C.; alternatively, from about 100° C. to about 250° C.; or alternatively, from about 180° C. to about 280° C. In these and other aspects, these temperature ranges also are meant to encompass circumstances where the pre-drying step is conducted at a series of different temperatures, instead of at a single fixed temperature, falling within the respective ranges.

The duration of the pre-drying step is not limited to any particular period of time. Typically, the pre-drying step may be conducted in a time period ranging from as little as 30-45 minutes to as long as 48-72 hours (or more), but more typically, the pre-drying step may be conducted in a time period that may be in a range from about 1 hour to about 72 hours, such as, for example, from about 1 hour to about 48 hours, from about 1 hour to about 36 hours, from about 2 hours to about 24 hours, or from about 2 hours to about 18 hours.

Alternatively, the pre-drying step may be conducted for a time period sufficient to reduce the moisture content of the spent catalyst to less than about 4 wt. %, less than about 2 wt. %, less than about 1 wt. %, less than about 0.5 wt. %, or less than about 0.1 wt. %. While not wishing to be bound by theory, it is believed that it may be beneficial to have substantially no moisture present when the chlorination step is begun to reduce corrosivity of the chlorine-containing stream on the reactor metallurgy. For instance, dry halogens and dry halogen acids are not corrosive and may be in employed in carbon steel environments, however, once moisture is present, even stainless steel may not be sufficient, and high alloy steels may be required.

Optionally, a method of regenerating a spent catalyst (e.g., comprising a transition metal and a catalyst support) comprising a chlorination step, followed by a carbon burn step, and then by a fluorination step, may further comprise a chlorine purging step prior to the carbon burn step. This purging step may comprise contacting the chlorinated spent catalyst with a chlorine purging stream comprising (or consisting essentially of, or consisting of) an inert gas. The inert gas may be helium, neon, argon, or nitrogen, or mixtures thereof; alternatively, helium; alternatively, neon; alternatively, argon; or alternatively, nitrogen.

Additionally, in some aspects, the chlorine purging stream may be substantially free of oxygen-containing compounds (e.g., oxygen and water), as discussed above in relation to the chlorination step. Hence, the chlorine purging step may be conducted in the presence of less than 100 ppmw of oxygen-containing compounds, or less than 50 ppmw, or less than 25 ppmw, or less than 10 ppmw, or less than 5 ppmw, or less than 3 ppmw.

Additionally, in some aspects, the chlorine purging stream may be substantially free of halogen-containing compounds, as discussed above in relation to the carbon burn step. Hence, the chlorine purging step may be conducted in the presence of less than 100 ppmw of halogen-containing compounds, or less than 50 ppmw, or less than 25 ppmw, or less than 10 ppmw, or less than 5 ppmw, or less than 3 ppmw.

The chlorine purging step may be performed at a chlorine purging temperature that generally may encompass the same temperature range as the chlorination temperature used in the chlorination step, but is not limited thereto. Accordingly, the chlorine purging temperature may be in a range from about 20° C. to about 500° C.; alternatively, from about 20° C. to about 400° C.; alternatively, from about 30° C. to about 300° C.; alternatively, from about 30° C. to about 250° C.; alternatively, from about 25° C. to about 150° C.; alternatively, from about 35° C. to about 300° C.; alternatively, from about 35° C. to about 200° C.; alternatively, from about 50° C. to about 250° C.; alternatively, from about 75° C. to about 250° C.; alternatively, from about 100° C. to about 300° C.; alternatively, from about 100° C. to about 250° C.; or alternatively, from about 150° C. to about 275° C. In these and other aspects, these temperature ranges also are meant to encompass circumstances where the chlorine purging step is conducted at a series of different temperatures, instead of at a single fixed temperature, falling within the respective ranges.

The duration of the chlorine purging step is not limited to any particular period of time. Typically, the chlorine purging step may be conducted in a time period ranging from as little as 30-45 minutes to as long as 48-72 hours (or more), but more typically, the chlorine purging step may be conducted in a time period that may be in a range from about 1 hour to about 48 hours, such as, for example, from about 1 hour to about 36 hours, from about 2 hours to about 36 hours, from about 2 hours to about 24 hours, or from about 2 hours to about 18 hours.

Alternatively, the chlorine purging step may be conducted for a time period sufficient to reduce the chlorine content of the outgoing purging effluent stream, after contacting the chlorinated spent catalyst, to less than 100 ppmw of chlorine-containing compounds (i.e., substantially chlorine-free). In some aspects consistent with the disclosure herein, the chlorine content of the outgoing chlorine purging effluent stream, after contacting the chlorinated spent catalyst, may be less than 50 ppmw, less than 25 ppmw, less than 10 ppmw, less than 5 ppmw, or less than 3 ppmw. While not wishing to be bound by theory, it is believed that it may be beneficial to have chlorine closely associated with the catalyst during the carbon burn step, but substantially no chlorine present in the free volume of the atmosphere surrounding the chlorinated spent catalyst (e.g., in the vessel containing the spent catalyst).

In various aspects contemplated herein, the methods of regenerating a spent catalyst may further include an optional oxygen purging step after the carbon burn step, but prior to the fluorination step. This oxygen purging step may comprise contacting the de-coked catalyst with an oxygen purging stream comprising (or consisting essentially of, or consisting of) an inert gas. The inert gas may be helium, neon, argon, or nitrogen, or mixtures thereof; alternatively, helium; alternatively, neon; alternatively, argon; or alternatively, nitrogen.

Additionally, in some aspects, the oxygen purging stream may be substantially free of oxygen-containing compounds (e.g., oxygen or water), as discussed above in relation to the chlorine purging step. Hence, the oxygen purging step may be conducted in the presence of less than 100 ppmw of oxygen-containing compounds, or less than 50 ppmw, or less than 25 ppmw, or less than 10 ppmw, or less than 5 ppmw, or less than 3 ppmw.

Additionally, in some aspects, the oxygen purging stream may be substantially free of halogen-containing compounds, as discussed above in relation to the chlorine purging step. Hence, the oxygen purging step may be conducted in the presence of less than 100 ppmw of halogen-containing compounds, or less than 50 ppmw, or less than 25 ppmw, or less than 10 ppmw, or less than 5 ppmw, or less than 3 ppmw.

The oxygen purging step may be performed at an oxygen purging temperature that generally may encompass the same temperature range as the chlorine purging temperature. Accordingly, the oxygen purging temperature may be in a range from about 0° C. to about 500° C.; alternatively, from about 25° C. to about 400° C.; alternatively, from about 30° C. to about 300° C.; alternatively, from about 30° C. to about 250° C.; alternatively, from about 35° C. to about 150° C.; alternatively, from about 40° C. to about 300° C.; alternatively, from about 45° C. to about 200° C.; alternatively, from about 50° C. to about 250° C.; alternatively, from about 75° C. to about 250° C.; alternatively, from about 100° C. to about 300° C.; alternatively, from about 100° C. to about 250° C.; or alternatively, from about 150° C. to about 275° C. In these and other aspects, these temperature ranges also are meant to encompass circumstances where the oxygen purging step is conducted at a series of different temperatures, instead of at a single fixed temperature, falling within the respective ranges.

The duration of the oxygen purging step is not limited to any particular period of time. Typically, the oxygen purging step may be conducted in a time period ranging from as little as 30-45 minutes to as long as 48-72 hours (or more), but more typically, the oxygen purging step may be conducted in a time period that may be in a range from about 1 hour to about 48 hours, such as, for example, from about 1 hour to about 36 hours, from about 2 hours to about 36 hours, from about 2 hours to about 24 hours, or from about 2 hours to about 18 hours.

Alternatively, the oxygen purging step may be conducted for a time period sufficient to reduce the oxygen content of the outgoing purging effluent stream, after contacting the de-coked catalyst, to less than 100 ppmw of oxygen-containing compounds (i.e., substantially oxygen-free). In some aspects consistent with the disclosure herein, the oxygen content of the outgoing oxygen purging effluent stream, after contacting the de-coked catalyst, may be less than 50 ppmw, less than 25 ppmw, less than 10 ppmw, less than 5 ppmw, or less than 3 ppmw.

In various aspects contemplated herein, the methods of regenerating a spent catalyst may further include an optional drying and/or calcining step after the fluorination step. If both drying and calcining are performed, typically the fluorinated catalyst is dried and then calcined.

If a drying step is performed, the drying step usually involves subjecting the fluorinated catalyst to conditions sufficient to reduce the solvent (e.g., water) content of the fluorinated catalyst to less than any desired residual solvent content, for example, less than 15 wt. %, less than 12 wt. %, less than 10 wt. %, or less than 8 wt. % solvent, based on the weight of the catalyst. Illustrative and non-limiting ranges for the amount of residual solvent after drying include from about 2 to about 15 wt. %, from about 4 to about 12 wt. %, from about 3 to about 8 wt. %, or from about 6 to about 12 wt. %, based on the weight of the catalyst.

The conditions used during the drying step encompass a wide range of drying times, drying temperatures, and drying pressures. For example, the drying time may range from about 1 to about 48 hours, from about 2 to about 24 hours, or from about 2 to about 12 hours, and the drying temperature may range from about 15° C. to about 200° C., from about 25° C. to about 150° C., or from about 50° C. to about 125° C. The drying pressure may be at or around atmospheric pressure, but in many instances, the drying step may be conducted under vacuum conditions at a sub-atmospheric pressure, such as less than 100 torr (13.3 kPa), less than 50 (6.67 kPa) torr, or less than 10 torr (1.33 kPa).

The drying step may be conducted using any suitable technique and equipment, whether batch or continuous. For instance, the drying step may comprise drying stationary fluorinated catalyst; alternatively, the drying step may comprise fluidizing the fluorinated catalyst while drying; or alternatively, the drying step may comprise drying the fluorinated catalyst in a rotary dryer. As would be recognized by those of skill in the art, other suitable techniques and equipment may be employed for the drying step, and such techniques and equipment are encompassed herein.

If a calcining step is performed after the fluorination step, the calcining step may be conducted at a variety of temperatures and time periods. Typical peak calcining temperatures often fall within a range from about 200° C. to about 800° C., such as from about 250° C. to about 600° C., from about 300° C. to about 600° C., or from about 300° C. to about 500° C. In these and other aspects, these temperature ranges also are meant to encompass circumstances where the calcination step is conducted at a series of different temperatures (e.g., an initial calcination temperature, a peak calcination temperature), instead of at a single fixed temperature, falling within the respective ranges. For instance, the calcination step may start at an initial temperature that is the same as the drying temperature in the drying step. Subsequently, the temperature of the calcination may be increased to a peak calcining temperature, for example, in a range from about 250° C. to about 600° C.

The duration of the calcining step is not limited to any particular period of time. Hence, the calcining step may be conducted, for example, in a time period ranging from as little as 30-45 minutes to as long as 36-48 hours, or more. The appropriate calcining time may depend upon, for example, the initial/peak calcining temperature and whether a drying step is used, among other variables. Generally, however, the calcining step may be conducted in a time period that may be in a range from about 30 minutes to about 48 hours, such as, for example, from about 1 hour to about 24 hours, from about 1 hour to about 12 hours, from about 2 hours to about 12 hours, or from about 2 hours to about 8 hours.

The calcining step may be conducted in a calcining gas stream that comprises (or consists essentially of, or consists of) an inert gas (e.g., nitrogen), oxygen, air, or any mixture or combination thereof. In some aspects, the calcining gas stream may comprise air, while in other aspects, the calcining gas stream may comprise a mixture of air and nitrogen. Yet, in certain aspects, the calcining gas stream may be an inert gas, such as nitrogen and/or argon.

The calcining step may be conducted using any suitable technique and equipment, whether batch or continuous. For instance, the calcining step may be performed in a belt calciner or, alternatively, a rotary calciner. In some aspects, the calcining step may be performed in a batch or continuous calcination vessel comprising a fluidized bed. As would be recognized by those of skill in the art, other suitable techniques and equipment may be employed for the calcining step, and such techniques and equipment are encompassed herein.

In an aspect, the method of regenerating a spent catalyst may be an in situ process, i.e., steps (1)-(3) may be performed in the same vessel system. However, in an alternate aspect, the fluorination step—step (3)—may be conducted in another vessel and/or location from that used for the chlorination and decoking steps.

In an aspect, step (1) may be performed by contacting a moving bed of the spent catalyst with the chlorine-containing stream, and the flow direction of the chlorine-containing gas stream relative to that of the spent catalyst may be concurrent or countercurrent. Alternatively, a fixed bed or a fluidized bed of the spent catalyst may be contacted with the chlorine-containing gas stream. In another aspect, the flow direction of the decoking gas stream in step (2) may be the same direction relative to the catalyst as that of the chlorine-containing gas stream, or the flow direction of the decoking gas stream may be in the opposite direction. In yet another aspect, the flow direction of the fluorine-containing solution in step (3) may be the same direction relative to the catalyst as that of the decoking gas stream, or the flow direction of the fluorine-containing solution may be in the opposite direction.

The methods of regenerating a spent catalyst disclosed herein may further comprise a reducing step (or reactivating step) after the fluorination step, thereby forming a reactivated catalyst. This reducing step may comprise contacting the fluorinated catalyst (or the calcined fluorinated catalyst) with a reducing gas stream comprising molecular hydrogen. In addition to molecular hydrogen, the reducing gas stream may comprise an inert gas, i.e., the reducing gas stream may comprise (or consist essentially of, or consist of) molecular hydrogen and an inert gas. Typical inert gasses useful in the reducing step may encompass helium, neon, argon, nitrogen, and the like, and this includes combinations of two or more of these materials. In certain aspects, the reducing gas stream may comprise (or consist essentially of, or consist of) molecular hydrogen and nitrogen.

In some aspects, molecular hydrogen may be the major component of the reducing gas stream, while in other aspects, molecular hydrogen may be a minor component. For example, the reducing gas stream may comprise at least about 25 mole % molecular hydrogen, at least about 35 mole % molecular hydrogen, at least about 50 mole % molecular hydrogen, at least about 65 mole % molecular hydrogen, at least about 75 mole % molecular hydrogen, or 100 mole % molecular hydrogen. Accordingly, suitable ranges for the mole % of molecular hydrogen in the reducing gas stream may include, but are not limited to, the following ranges: from about 25 to 100 mole %, from about 50 to 100 mole %, from about 25 to 100 mole %, from about 35 to 100 mole %, from about 55 to 100 mole %, from about 25 to about 75 mole %, from about 35 to about 65 mole %, or from about 70 to 100 mole %, and the like.

The reducing step may be conducted at a variety of temperatures and time periods. For instance, the reducing step may be conducted at a peak reducing temperature in a range from about 300° C. to about 600° C.; alternatively, from about 300° C. to about 550° C.; alternatively, from about 400° C. to about 600° C.; alternatively, from about 350° C. to about 575° C.; alternatively, from about 400° C. to about 550° C.; or alternatively, from about 450° C. to about 550° C. In these and other aspects, these temperature ranges also are meant to encompass circumstances where the reducing step is conducted at a series of different temperatures (e.g., an initial reducing temperature, a peak reducing temperature), instead of at a single fixed temperature, falling within the respective ranges. For instance, the reducing step may start at an initial reducing temperature which is the same as the drying temperature or the calcination temperature. Subsequently, the temperature of the reducing step may be adjusted to a peak reducing temperature, for example, in a range from about 400° C. to about 600° C.

The duration of the reducing step is not limited to any particular period of time. Hence, the reducing step may be conducted, for example, in a time period ranging from as little as 1 hour to as long as 48-72 hours, or more. For example, the reducing step may be conducted in a time period that may be in a range from about 2 hours to about 48 hours, from about 3 hours to about 36 hours, from about 5 hours to about 36 hours, from about 2 hours to about 30 hours, or from about 10 hours to about 30 hours.

In some aspects, the method of regenerating the catalyst may further comprise a step of reducing the catalyst after step (3). For instance, the reducing step as described herein may be conducted after the fluorination step, and the reducing step may be performed in the same vessel system as that of steps (1)-(3). Alternatively, in an ex situ process, the reducing step may be performed in the same vessel system as that of steps (1)-(2), or in the same vessel system as that of fluorination step (3).

In further aspects, the reactivated or regenerated catalyst may have an activity from about 50% to about 100%, or from about 70% to about 100%, of the catalyst activity of a fresh reference catalyst of the same production run of catalyst, when tested on the same equipment, and under the same method and test conditions. For instance, the reactivated or regenerated catalyst may have substantially the same activity as that of the fresh reference catalyst (i.e., a temperature within 10° F. of the temperature required by the fresh catalyst to achieve an aromatics yield of 63 wt. % in $C_5^+$, as described in the examples that follow). Further, in some aspects, the regenerated catalyst may have a temperature within 5° F. of the temperature required by the fresh catalyst to achieve an aromatics yield of 63 wt. % in $C_5^+$.

Additionally or alternatively, the reactivated or regenerated catalyst may have a selectivity from about 70% to about 105%, from about 85% to about 100%, or from about 98% to about 105%, of the catalyst selectivity of a fresh reference catalyst of the same production run of catalyst, when tested on the same equipment, and under the same method and test conditions.

If desired, the spent catalyst—at any stage during the regeneration process—may be screened to remove fines such as small catalyst particles, and chunks such as agglomerations of catalyst and coke. For example, screening of the catalyst may be conducted prior to contacting with the chlorine-containing stream, prior contacting with the decoking gas stream, prior to contacting with the fluorine-containing solution, and/or after step (3).

Reforming Processes with Aromatization Catalysts

Also encompassed herein are various processes for reforming hydrocarbons. One such reforming process may comprise (or consist essentially of, or consist of):

(A) contacting a hydrocarbon feed with an aromatization catalyst comprising a transition metal and a catalyst support under reforming conditions in a reactor system to produce an aromatic product;

(B) performing step (A) for a time period sufficient to form a spent catalyst;

(C) contacting the spent catalyst with a chlorine-containing stream comprising a chlorine-containing compound to produce a chlorinated spent catalyst;

(D) contacting the chlorinated spent catalyst with a decoking gas stream comprising oxygen to produce a de-coked catalyst; and (E) contacting the de-coked catalyst with a fluorine-containing solution comprising a fluorine-containing compound.

Generally, the features of any of the reforming processes disclosed herein (e.g., the hydrocarbon feed, the aromatization catalyst, the transition metal, the catalyst support, the reforming conditions, the fluorine-containing solution comprising the fluorine-containing compound, the conditions under which the fluorination step is conducted, the chlorine-containing gas stream, the conditions under which the chlorination step is conducted, the decoking gas stream, and the conditions under which the decoking step is conducted, among others) are independently described herein, and these features may be combined in any combination to further describe the disclosed reforming processes. Moreover, other process steps may be conducted before, during, and/or after any of the steps listed in the disclosed reforming processes, unless stated otherwise.

The chlorination, carbon burn, and fluorination steps (steps (C)-(E)) are discussed herein above. Any aspects and features of the chlorination step and/or the carbon burn step and/or the fluorination step (as well as other steps that may be conducted before, during and/or after the chlorination step and/or the carbon burn step and/or the fluorination step) described herein may be utilized in the processes for reforming hydrocarbons and, accordingly, are encompassed herein.

In these reforming processes, step (A) may comprise contacting a hydrocarbon feed with an aromatization catalyst under reforming conditions in a reactor system to produce an aromatic product. The reactor systems for reforming and the respective reforming conditions are well known to those of skill in the art and are described, for example, in U.S. Pat. Nos. 4,456,527, 5,389,235, 5,401,386, 5,401,365, 6,207,042, and 7,932,425, the disclosures of which are incorporated herein by reference in their entirety.

Likewise, typical hydrocarbon feeds are disclosed in these references. Often, the hydrocarbon feed may be a naphtha stream or light naphtha stream. In certain aspects, the hydrocarbon feed may comprise $C_6$-$C_8$ alkanes and/or cycloalkanes (e.g., hexane, heptane, cyclohexane, and methylcyclohexane, among others).

Step (B) in the reforming processes indicates that step (A) may be performed for a time period sufficient for the aromatization catalyst to become "spent." As discussed herein above, a "spent" catalyst is typically a catalyst that has unacceptable performance in one or more of catalyst activity, hydrocarbon feed conversion, yield to a desired product(s), selectivity to a desired product(s), or an operating parameter, such as maximum operating temperature or pressure drop across a reactor, although not limited thereto. Once the aromatization catalyst is "spent," the regeneration steps (C), (D), and (E), amongst others, may be performed.

In an aspect, the reforming process may be an in situ process, i.e., steps (A)-(E) may be performed in the same reactor system. However, in an alternate aspect, the catalyst regeneration steps (C)-(E) may be conducted externally to the reforming reactor system, such as in another vessel and/or location. For instance, the chlorination, carbon burn, and fluorination steps may be conducted in a vessel that is not in the reforming reactor system. In yet another aspect, fluorination step (E) may be conducted externally to the reactor system of any of steps (A)-(D). For example, the fluorination step may be conducted in a vessel different from that used in any of steps (A)-(D).

In an aspect, step (C) may be performed by contacting a moving bed of the spent catalyst with the chlorine-containing gas stream, and the flow direction of the chlorine-containing gas stream relative to that of the spent catalyst may be concurrent or countercurrent. Alternatively, a fixed bed or a fluidized bed of the spent catalyst may be contacted with the chlorine-containing gas stream. In another aspect, the flow direction of the decoking gas stream in step (D) may be the same direction relative to the catalyst as that of the chlorine-containing gas stream, or the flow direction of the decoking gas stream may be in the opposite direction. In yet another aspect, the flow direction of the fluorine-containing solution in step (E) may be the same direction relative to the catalyst as that of the decoking gas stream, or the flow direction of the fluorine-containing solution may be in the opposite direction.

If desired, the spent catalyst—at any stage during the regeneration steps—may be screened to remove fines such as small catalyst particles, and chunks such as agglomerations of catalyst and coke. For example, screening of the catalyst may be conducted prior to the chlorination step, after the carbon burn step, prior to fluorination step, and/or after step (E).

In some aspects, the reforming process may further comprise a step of reducing (reactivating) the catalyst after step (E). For instance, the reducing step as described herein may be conducted after the fluorination step, and the reducing step may be performed in the same reactor system as that of steps (A)-(E). Alternatively, in an ex situ process, the reducing or reactivating step may be performed in the same reforming reactor system as that of step (A), or alternatively, in the same vessel as that of fluorination step (E).

Any catalysts reactivated or regenerated by the methods disclosed herein are considered within the scope of this disclosure and encompassed herein. In some aspects, the reactivated or regenerated catalyst may have from about 50% to about 100%, or from about 70% to about 100%, of the catalyst activity of a fresh reference catalyst of the same production run of catalyst, tested on the same equipment, and under the same method and test conditions. For instance, the reactivated or regenerated catalyst may have substantially the same activity as that of the fresh reference catalyst.

Additionally or alternatively, the reactivated or regenerated catalyst may have a selectivity from about 70% to about 105%, from about 85% to about 100%, or from about 98% to about 105%, of the catalyst selectivity of a fresh reference catalyst of the same production run of catalyst, tested on the same equipment, and under the same method and test conditions.

Transition Metal Based Catalysts

Consistent with aspects disclosed herein, and the various methods described herein above and below, the aromatization catalyst (fresh, spent, regenerated, or reactivated) may comprise a transition metal and a catalyst support. The catalyst support typically may comprise an inorganic oxide, examples of which may include, but are not limited to, bound medium and/or large pore zeolites (aluminosilicates), amorphous inorganic oxides, as well as mixtures thereof. Large pore zeolites often may have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often may have average pore diameters in a range of from about 5 Å to about 7 Å. Amorphous inorganic oxides may include, but are not limited to, aluminum oxide, silicon oxide, titania, and combinations thereof.

The term "zeolite" generally refers to a particular group of hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms may be equal to 2. The framework exhibits a negative electrovalence that typically may be balanced by the inclusion of cations within the crystal, such as metals, alkali metals, alkaline earth metals, and/or hydrogen.

In some aspects, the catalyst support may comprise an L-type zeolite. L-type zeolite supports are a sub-group of zeolitic supports, which may contain mole ratios of oxides in accordance with the formula: $M_{2/n}OAl_2O_3xSiO_2yH_2O$. In this formula, "M" designates an exchangeable cation (one or more) such as barium, calcium, cerium, lithium, magnesium, potassium, sodium, strontium, cesium, and/or zinc, as well as non-metallic cations like hydronium and ammonium ions, which may be replaced by other exchangeable cations without causing a substantial alteration of the basic crystal structure of the L-type zeolite. The "n" in the formula represents the valence of "M"; "x" is 2 or greater; and "y" is the number of water molecules contained in the channels or interconnected voids of the zeolite.

In one aspect, the catalyst support may comprise a bound potassium L-type zeolite, also referred to as a KL-zeolite, while in another aspect, the catalyst support may comprise a barium ion-exchanged L-zeolite. As used herein, the term "KL-zeolite" refers to L-type zeolites in which the principal cation M incorporated in the zeolite is potassium. A KL-zeolite may be cation-exchanged (e.g., with barium or cesium) or impregnated with a transition metal and one or more halides to produce a transition metal impregnated, halided zeolite or a KL supported transition metal-halide zeolite catalyst.

The aromatization catalyst (fresh, spent, regenerated, or reactivated) comprises a catalyst support, which may comprise a binder and the zeolite. Non-limiting examples of the binder may include silica, alumina, magnesia, boria, titania, zirconia, various clays, and the like, including mixed oxides thereof, as well as mixtures thereof. For example, the catalyst support may comprise a binder comprising alumina, silica, a mixed oxide thereof, or a mixture thereof. In other aspects, the catalyst support may comprise a KL-zeolite and a binder comprising alumina, silica, a mixed oxide thereof, or a mixture thereof. The zeolite may be bound with the binder using any method known in the art.

The aromatization catalyst may comprise a transition metal, and non-limiting examples of suitable transition metals may include iron, cobalt, nickel, ruthenium, rhodium, rhenium, palladium, osmium, iridium, platinum, gold, silver, copper, and the like, or a combination of two or more transition metals. In one aspect, the transition metal may comprise a Group 8-11 transition metal or a Group 8-10 transition metal (one or more), while in another aspect, the transition metal may comprise platinum (Pt).

In one aspect, the catalyst (fresh, spent, regenerated, or reactivated) may comprise from about 0.1 wt. % to about 10 wt. % transition metal. In another aspect, the catalyst may comprise from about 0.3 wt. % to about 5 wt. % transition metal. In yet another aspect, the catalyst may comprise from about 0.3 wt. % to about 3 wt. % transition metal, or from about 0.5 wt. % to about 2 wt. % transition metal. These weight percentages are based on the weight of the "dry" catalyst, excluding any weight attributable to carbon.

In circumstances where the transition metal comprises platinum, the catalyst (fresh, spent, regenerated, or reactivated) may comprise from about 0.1 wt. % to about 10 wt. % platinum; alternatively, from about 0.3 wt. % to about 5 wt. % platinum; alternatively, from about 0.3 wt. % to about 3 wt. % platinum; or alternatively, from about 0.5 wt. % to about 2 wt. % platinum. In a particular aspect contemplated herein, the catalyst may comprise platinum and a catalyst support comprising a KL-zeolite.

While not being limited thereto, the catalyst support may comprise from about 5 wt. % to about 35 wt. % of a binder. For example, the catalyst support may comprise from about 5 wt. % to about 30 wt. %, or from about 10 wt. % to about 30 wt. % the binder. Similar to above, these weight percentages are based on the weight of the catalyst support excluding any weight contribution due to carbon.

In an aspect, the aromatization catalyst (fresh, spent, regenerated, or reactivated) may further comprise a halogen, such as chlorine, fluorine, bromine, iodine, or a combination of two or more halogens. For example, the catalyst may comprise chlorine, or fluorine, or both chlorine and fluorine. Chlorine may be present in the catalyst in an amount of from about 0.01 wt. % to about 5 wt. %, from 0.01 wt. % to about 3 wt. %, or from 0 wt. % to about 2 wt. %. Likewise, the catalyst may comprise from about 0.01 wt. % to about 5 wt. % fluorine, from about 0.01 wt. % to about 3 wt. % fluorine, or from 0 wt. % to about 2 wt. % fluorine. These weight percentages are based on the weight of the dry catalyst, and exclude any weight contribution due to carbon. In some aspects, a fresh, regenerated, or reactivated catalyst may contain from about 0.5 wt. % to about 3 wt. % each of chlorine and fluorine. However, the spent catalyst may have little to no halogen left prior to the regeneration process.

Consistent with aspects of this invention in which the catalyst (fresh, spent, or rejuvenated) comprises both chlorine and fluorine, typically the molar ratio of chlorine:fluorine may be in the range of from about 0.2:1 to about 4:1. Other suitable molar ratios of Cl:F may include the following non-limiting ranges: from about 0.3:1 to about 4:1, from about 0.5:1 to about 4:1, from about 0.3:1 to about 3:1, from about 0.3:1 to about 2:1, or from about 0.5:1 to about 2.5:1.

Examples of representative and non-limiting catalysts that are encompassed herein include those disclosed in U.S. Pat. Nos. 5,196,631, 6,190,539, 6,406,614, 6,518,470, 6,812,180, 7,153,801, and 7,932,425, the disclosures of which are incorporated herein by reference in their entirety.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

In each of the examples, the following standard testing procedures were utilized. The catalysts were ground and sieved to 25-45 mesh, and 1 cc of the sieved catalyst was placed in a ⅜-inch OD stainless steel reactor vessel in a temperature controlled furnace. After reducing the catalyst under flowing molecular hydrogen, a feed stream of aliphatic hydrocarbons and molecular hydrogen was introduced to the reactor vessel at a pressure of 100 psig, a $H_2$:hydrocarbon molar ratio of 1.3:1, and a liquid hourly space velocity (LHSV) of 12 $hr^{-1}$ to obtain catalyst performance data over time. The aliphatic hydrocarbon feed contained approximately 0.61 mole fraction of convertible $C_6$ species and 0.21 mole fraction of convertible $C_7$ species. The balance was attributed to aromatics, $C_8^+$, and highly branched isomers, which are classified as non-convertibles. The reactor effluent composition was analyzed by gas chromatography to determine the total aromatics and the aromatics selectivity.

Catalyst activity was quantified by the temperature needed to obtain a defined aromatics yield of 63 wt. % in $C_5^+$. The temperatures were then plotted versus time to evaluate catalyst activity performance over time. Lower temperatures, therefore, demonstrate a more active catalyst. Selectivity to aromatics (mol/mol) was calculated and also used to compare catalyst selectivity over time.

Examples 1-3

Figure 2:
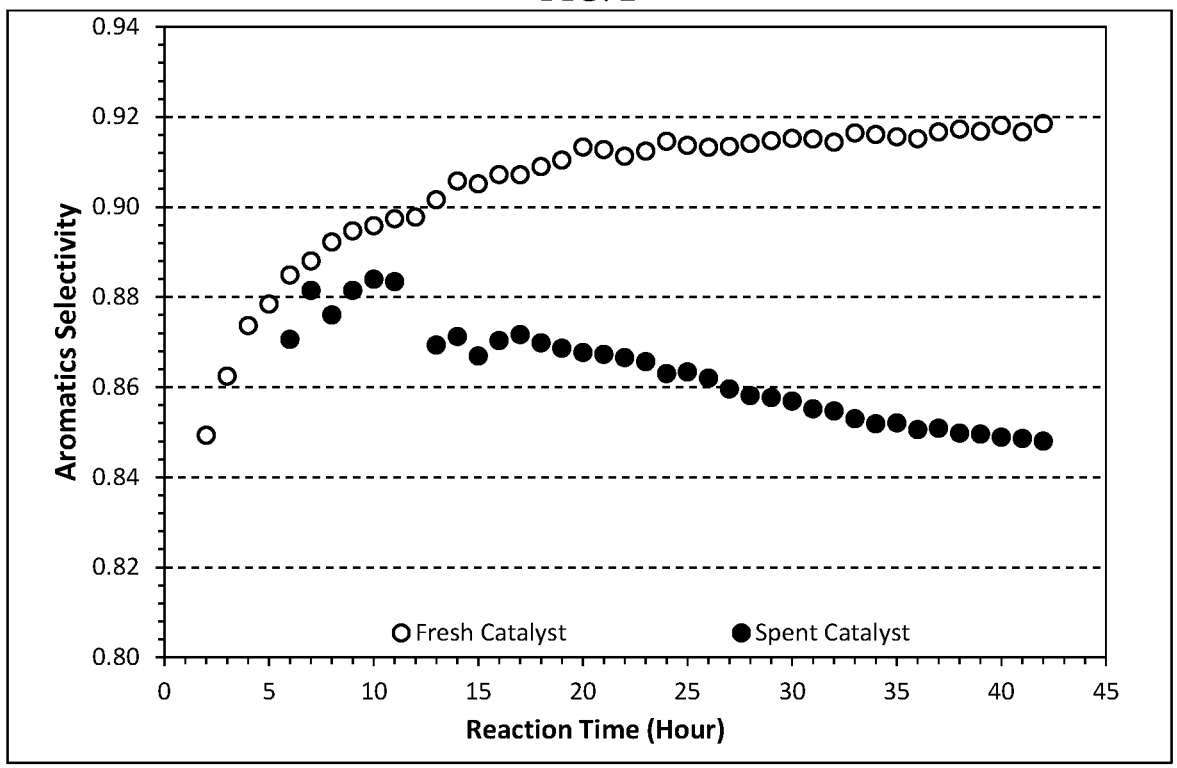
FIG. 2 presents a plot of the aromatics selectivity versus reaction time for the fresh catalyst and the spent catalyst.

In Examples 1-3, experiments were conducted to demonstrate the effectiveness of various processes and steps in regenerating a spent catalyst, with the performance of a fresh aromatization catalyst used as a target baseline. The fresh aromatization catalyst was a Pt/KL-zeolite containing approximately 1 wt. % platinum, 0.83 wt. % Cl, and 0.84 wt. % F (determined via XRF), with a surface area of approximately 177 m²/g, a pore volume of 0.19 cc/g, and a micropore volume of 0.062 cc/g. The source of the spent catalyst was the fresh catalyst, but after it had been deactivated after long-term use in an aromatization process. Prior to usage in these examples, the spent catalyst was subjected to a mild partial decoking step to remove unreacted hydrocarbons and light carbonaceous deposits from the spent catalyst. Catalyst activity and catalyst selectivity data for the fresh catalyst and the spent catalyst are summarized in FIG. 1 and FIG. 2, respectively. The spent catalyst had poor catalyst activity; extremely high temperatures were needed to achieve 63 wt. % aromatics yield. The spent catalyst also had an unacceptable aromatics selectivity of less than 87%.

Example 1

Figure 3:
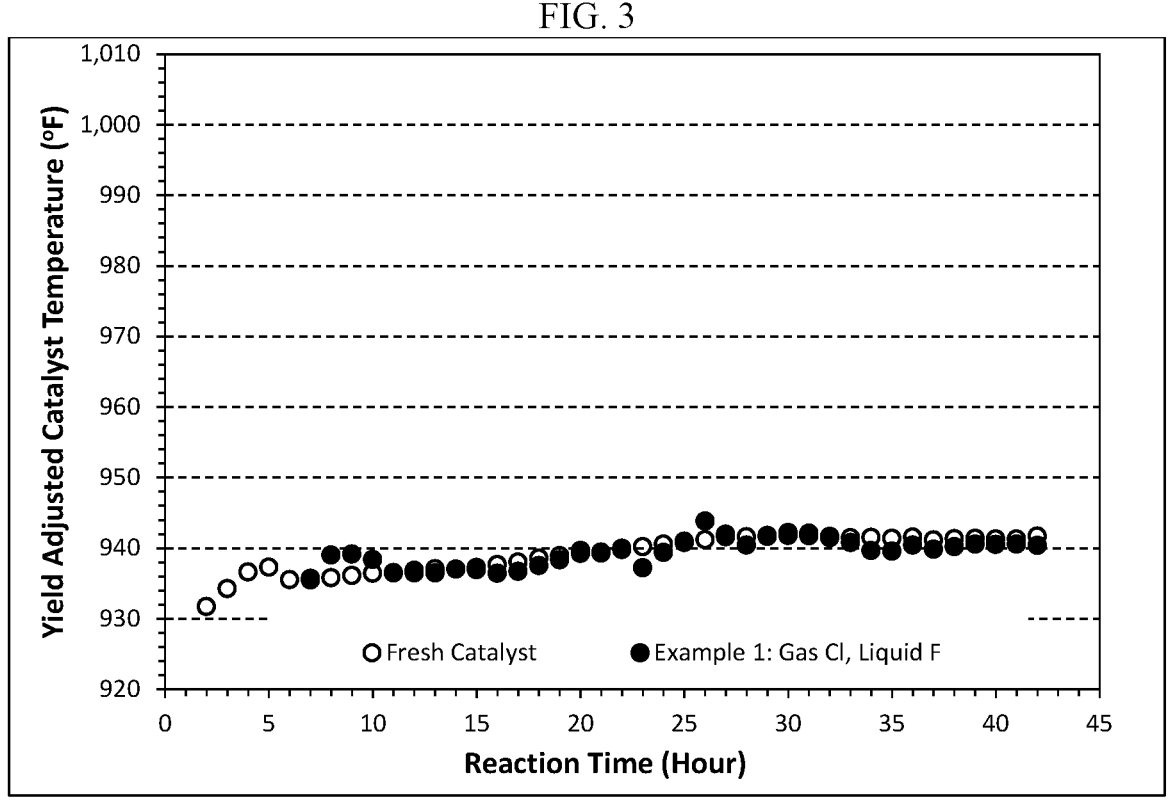
FIG. 3 presents a plot of the yield adjusted catalyst temperature versus reaction time for the regenerated catalyst of Example 1, compared with the fresh catalyst.
Figure 4:
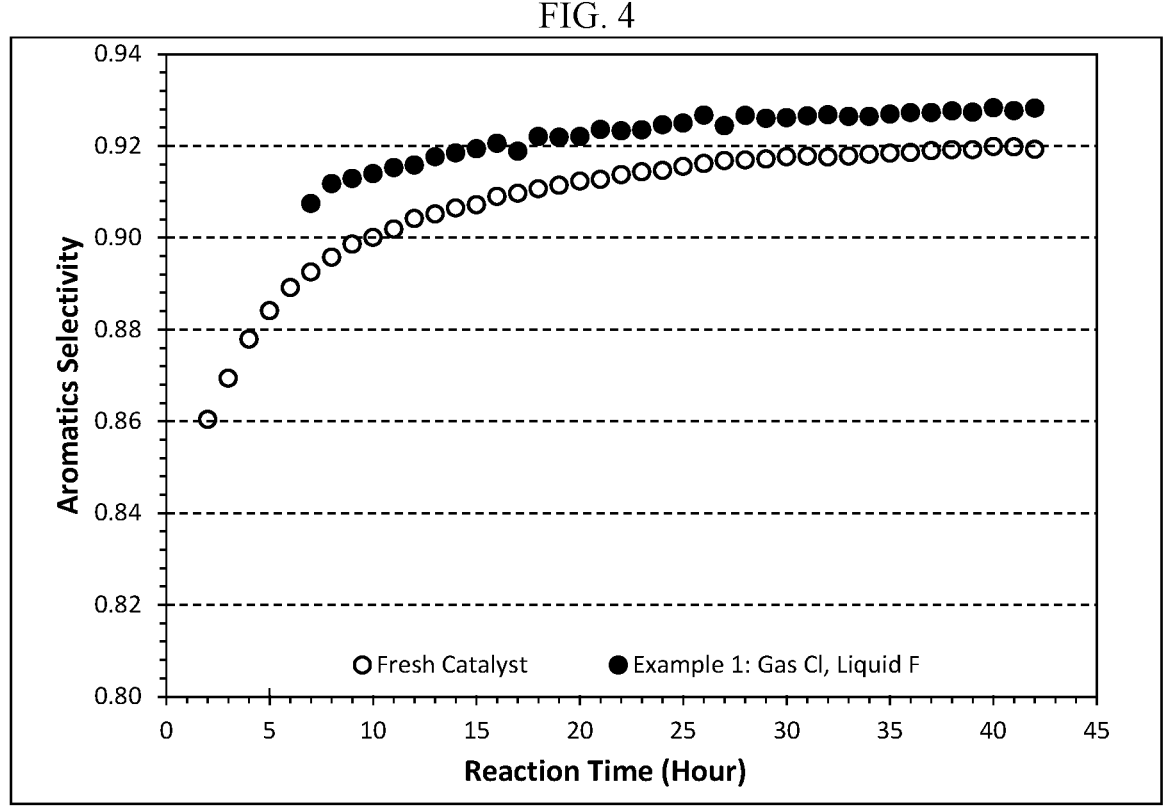
FIG. 4 presents a plot of the aromatics selectivity versus reaction time for the regenerated catalyst of Example 1, compared with the fresh catalyst.

The regeneration procedure for Example 1 was as follows. A spent catalyst was dried under nitrogen at 400° F. (204° C.) for 16 hours (GHSV=1500 hr⁻¹). Chlorine diluted in a nitrogen gas stream (0.9 vol. % Cl) was added to the dried spent catalyst at 300° F. (149° C.) over 3 hours. After the chlorination step was complete, the chlorinated spent catalyst was purged at 400° F. (204° C.) with nitrogen for 16 hours. After purging, nitrogen gas was replaced by a mixture of air and nitrogen (1 vol. % oxygen). The catalyst was heated up to 750° F. (340° C.) for 44 hours using a 0.8° F./min ramp (0.4° C./min). After the carbon burn step, fluorine was added in the liquid phase. First, 0.69 g of ammonium fluoride was dissolved into 13 mL of deionized water, then 38 g of the chlorinated and de-coked catalyst was impregnated with the fluorine-containing solution at ambient temperature, followed by resting the impregnated catalyst for 4 hours. The fluorinated catalyst was dried for 3 hours under vacuum at a maximum temperature of 95° C., followed by calcination at 900° F. (482° C.) in air for 1 hour. The regenerated catalyst was then tested in the aromatization reaction using the above procedure and the results are presented in FIGS. 3-4. FIG. 3 illustrates that full catalyst activity was returned to the catalyst using a regeneration procedure where a chlorine-containing compound was added in the gas phase as chlorine gas, following by de-coking in the absence of moisture or without the addition of a halogen to the decoking gas stream, followed by addition of a fluorine-containing compound added in the liquid phase as ammonium fluoride. Specifically, FIG. 3 shows that the same temperature was needed for both the fresh catalyst and the regenerated catalyst of Example 1 to achieve the same aromatics yield (63 wt. % in $C_5$) throughout the 40-hr experiment, indicating that the fresh catalyst and the regenerated catalyst of Example 1 had substantially the same catalyst activity. FIG. 4 illustrates that the catalyst selectivity of the regenerated catalyst was comparable to, or better than, that of the fresh catalyst using a regeneration procedure where a chlorine-containing compound was added in the gas phase as chlorine gas, following by de-coking in the absence of moisture or without the addition of a halogen to the decoking gas stream, followed by addition of a fluorine-containing compound added in the liquid phase as ammonium fluoride. Specifically, FIG. 4 shows aromatics selectivity in the 90-94% range for the regenerated catalyst of Example 1 throughout the 40-hr experiment, which was slightly better than that of the fresh catalyst.

Example 2

Figure 5:
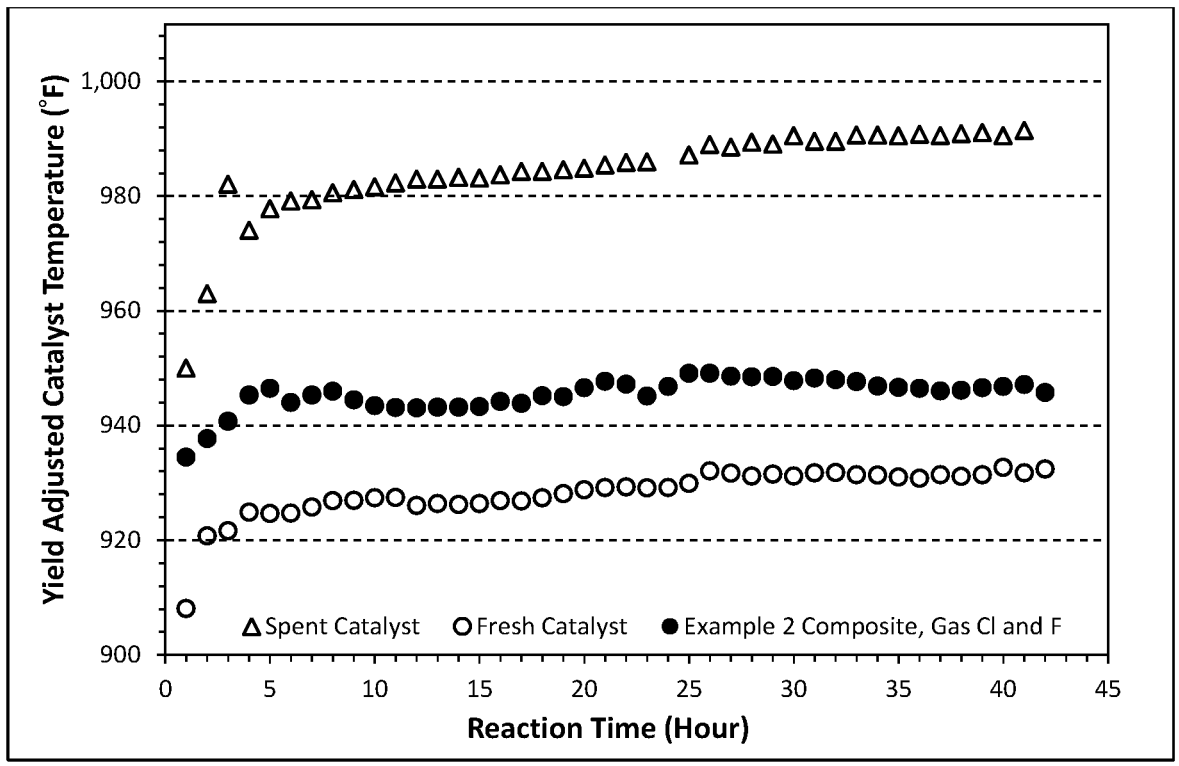
FIG. 5 presents a plot of the yield adjusted catalyst temperature versus reaction time for the regenerated catalyst of Comparative Example 2, compared with the fresh catalyst and the spent catalyst.
Figure 6:
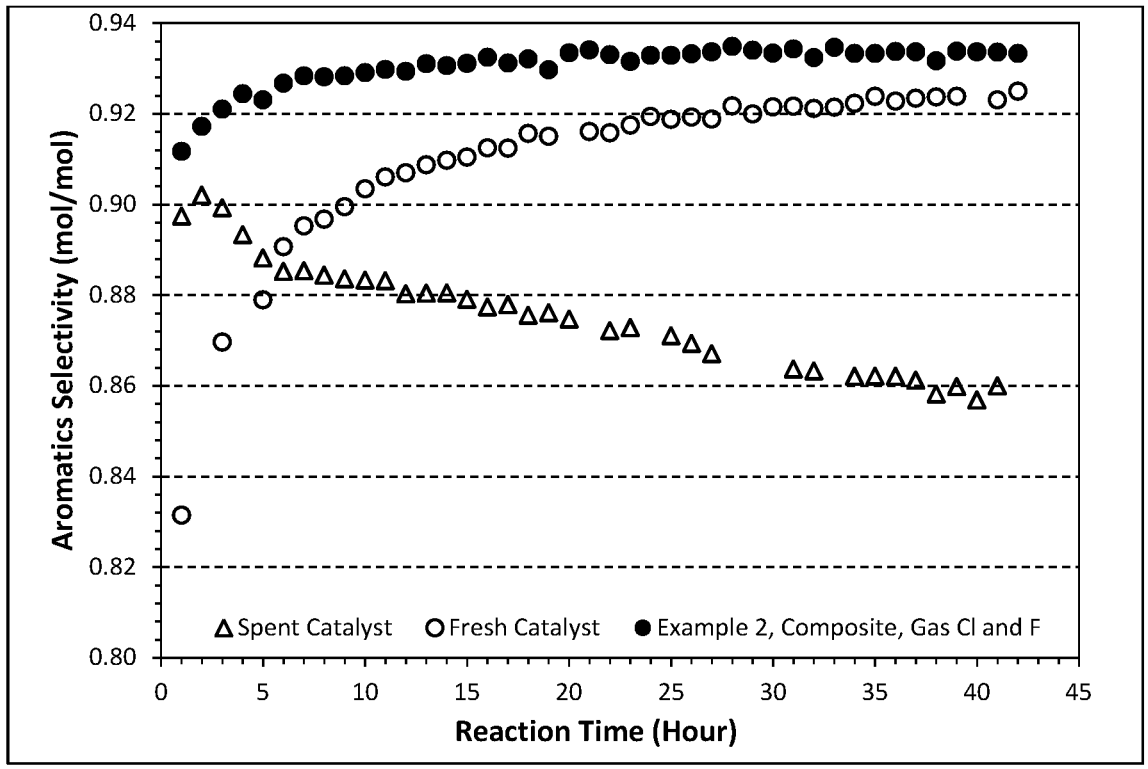
FIG. 6 presents a plot of the aromatics selectivity versus reaction time for the regenerated catalyst of Comparative Example 2, compared with the fresh catalyst and the spent catalyst.

For Comparative Example 2, both the chlorination and fluorination steps were performed in the vapor phase at ambient temperatures. As in Example 1, this procedure used a fixed bed reactor with chlorination occurring in the gas phase, but the chlorination temperature was 75° F. (24° C.). The chlorinated spent catalyst was purged with nitrogen while the temperature was raised to 400° F. (204° C.) and held for 16 hours. After purging, nitrogen gas was replaced by a mixture of air and nitrogen (1 vol. % oxygen), and the catalyst was heated up to 750° F. (340° C.) for 44 hours. The de-coked catalyst was allowed to cool to room temperature in the 1 vol. % oxygen in nitrogen gas flow. Fluorine diluted in a nitrogen gas stream (0.9 vol. % F) was added to the de-coked spent catalyst at 75° F. (24° C.) over 3 hours. After the fluorination step was complete, the fluorinated catalyst was purged with nitrogen while the temperature was raised to 400° F. (204° C.) and held for 16 hours The regenerated catalyst of Example 2 was then tested in the aromatization reaction using the above procedure and the results are presented in FIGS. 5-6. FIG. 5 illustrates that some catalyst activity was returned, but full catalyst activity was not restored to the catalyst using a regeneration procedure where a chlorine-containing compound and fluorine-containing compound were added in the gas phase at 75° F. (24° C.). Specifically, FIG. 5 shows that a higher temperature was needed for the regenerated catalyst of Example 2 to achieve the same aromatics yield (63 wt. % in $C_5^+$) as the fresh catalyst throughout the 40-hr experiment. FIG. 6 illustrates that catalyst selectivity of the regenerated catalyst was better than that of the fresh catalyst using the regeneration procedure of Example 2. Specifically, FIG. 6 shows aromatics selectivity in the 93% range for the regenerated catalyst of Example 2 throughout the 40-hr experiment, which was better than that of the fresh catalyst.

TABLE I

Halide distribution across the catalyst bed for Comparative Example 2.

| Layer | Cl (wt. %) | F (wt. %) |
| --- | --- | --- |
| 1 | 0.419 | 3.12 |
| 4 | 0.702 | 0.07 |

For Comparative Example 2, both chlorination and fluorination steps were performed in the vapor phase. However, upon analysis of the regenerated catalyst it was discovered that the chlorine and fluorine distribution throughout the catalyst bed in the fixed bed regeneration reactor was not uniform (see Table I). Layer 1 was the quarter of the catalyst bed that was closest to the entry point of the gaseous halides, and Layer 4 was the farthest quarter of the catalyst bed away from the entry point. Table I demonstrates a significant disadvantage to performing the entire regeneration procedure in the gas phase.

Example 3

Figure 7:
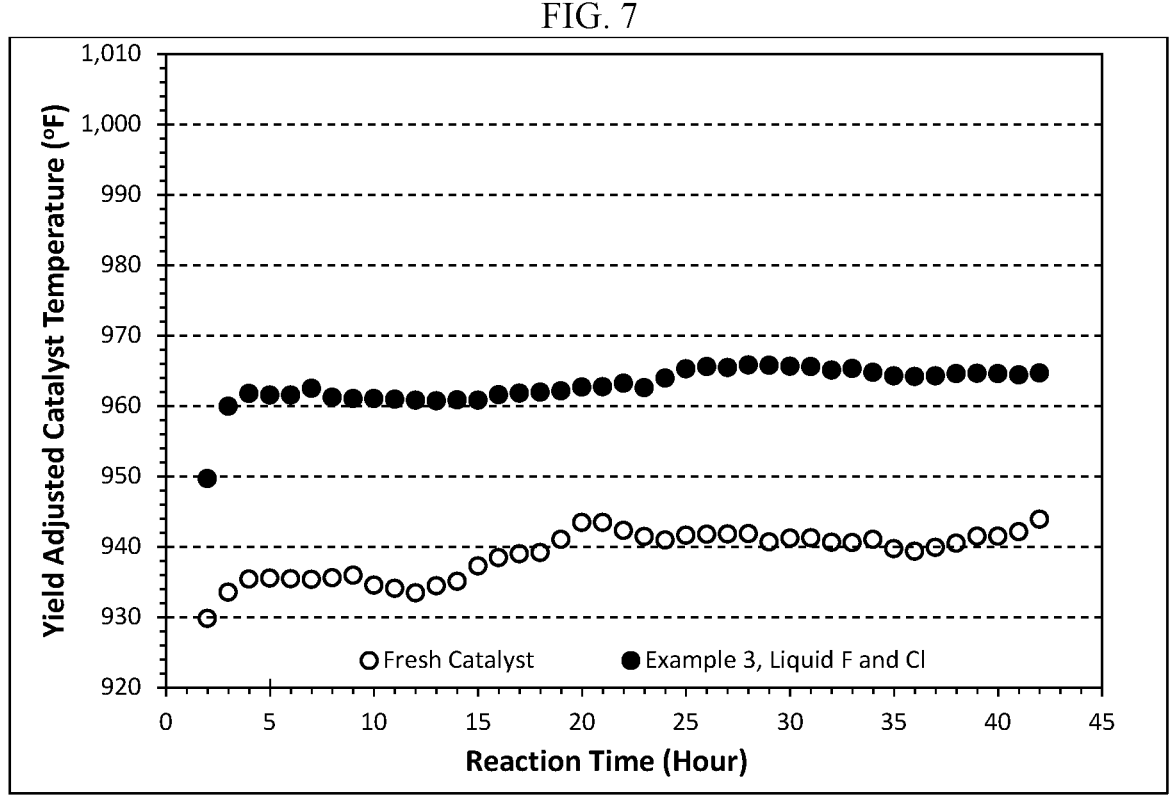
FIG. 7 presents a plot of the yield adjusted catalyst temperature versus reaction time for the regenerated catalyst of Comparative Example 3, compared with the fresh catalyst.
Figure 8:
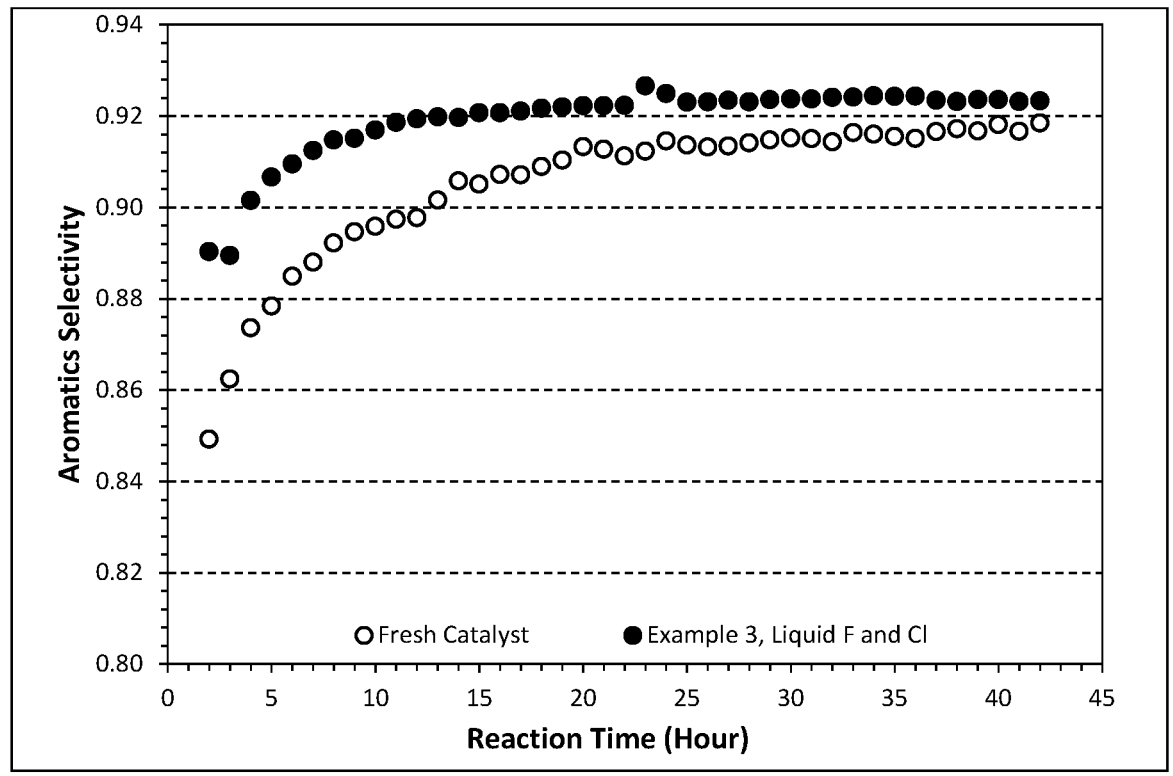
FIG. 8 presents a plot of the aromatics selectivity versus reaction time for the regenerated catalyst of Comparative Example 3, compared with the fresh catalyst.

For Comparative Example 3, both chlorination and fluorination steps were performed in the liquid phase. First, 1.43 g of ammonium chloride and 1.82 g of ammonium fluoride were dissolved in 30 mL of deionized water, then 100 g of the spent catalyst was impregnated with the chlorine/fluorine-containing solution. The impregnated material was then vacuum dried at a maximum temperature of 95° C., followed by calcination in air at 750° F. (340° C.) for 44 hours using a 0.8° F./min ramp (0.4° C./min). The regenerated catalyst of Comparative Example 3 was then tested in the aromatization reaction using the above procedure. FIGS. 7-8 demonstrate that selectivity was returned to the catalyst, but the activity was far less than that of the fresh catalyst (~20-25° F. higher temperatures were needed to achieve 63 wt. % aromatics yield), and the activity was far less than that of the regenerated catalyst of Example 1.

Catalyst properties of the fresh catalyst, spent catalyst, and regenerated catalysts of Examples 1-3 are summarized in Table II.

TABLE II

Catalyst property summary.

| Property | Spent Catalyst | Comparative Example 3 | Example 1 | Fresh Catalyst | Comparative Example 2 |
|---|---|---|---|---|---|
| Micropore volume (cc/g) | 0.040 | 0.038 | 0.030 | 0.062 | — |
| Pt Dispersion (%) | 45 | 38 | 48 | 67 | Layer 1: 20<br>Layer 4: 58 |
| Carbon (wt. %) | 1.3 | 0.01 | 0.02 | 0.01 | Layer 1: 0.08<br>Layer 4: 0.42 |
| Fluorine (wt. %) | 0.05 | 0.69 | 0.63 | 0.84 | Layer 1: 3.12<br>Layer 4: 0.07 |
| Chlorine (wt. %) | 0.18 | 0.89 | 0.89 | 0.83 | Layer 1: 0.42<br>Layer 4: 0.70 |

The invention is described above with reference to numerous aspects and specific examples. Many variations will suggest themselves to those skilled in the art in light of the above detailed description. All such obvious variations are within the full intended scope of the appended claims. Other aspects of the invention may include, but are not limited to, the following (aspects are described as "comprising" but, alternatively, may "consist essentially of" or "consist of"):

Aspect 1. A reforming method comprising:

(A) contacting a hydrocarbon feed with an aromatization catalyst comprising a transition metal and a catalyst support under reforming conditions in a reactor system to produce an aromatic product;

(B) performing step (A) for a time period sufficient to form a spent catalyst;

(C) contacting the spent catalyst with a chlorine-containing stream comprising a chlorine-containing compound to produce a chlorinated spent catalyst;

(D) contacting the chlorinated spent catalyst with a decoking gas stream comprising oxygen to produce a de-coked catalyst; and (E) contacting the de-coked catalyst with a fluorine-containing solution comprising a fluorine-containing compound to produce a fluorinated catalyst.

Aspect 2. The method defined in aspect 1, wherein the reforming method is an in situ process, for example, steps (A)-(E) are performed in the same reactor system.

Aspect 3. The method defined in aspect 1, wherein step (E) is performed externally to the reactor system of steps (A)-(D), for example, step (E) is performed in a vessel that is not in the reforming reactor system.

Aspect 4. The method defined in any of aspects 1-3, further comprising a step of reducing the catalyst after step (E).

Aspect 5. A method of regenerating a spent catalyst comprising a transition metal and a catalyst support, the method comprising:

(1) contacting the spent catalyst with a chlorine-containing stream comprising a chlorine-containing compound to produce a chlorinated spent catalyst;

(2) contacting the chlorinated spent catalyst with a decoking gas stream comprising oxygen to produce a de-coked catalyst; and (3) contacting the de-coked catalyst with a fluorine-containing solution comprising a fluorine-containing compound to produce a fluorinated catalyst.

Aspect 6. The method defined in any of the preceding aspects, wherein the fluorine-containing solution comprises (or consists essentially of, or consists of) the fluorine-containing compound and any solvent disclosed herein, for example, water or a hydrocarbon solvent.

Aspect 7. The method defined in any of the preceding aspects, wherein the fluorine-containing solution comprises (or consists essentially of, or consists of) water and at least one of ammonium fluoride and tetramethylammonium fluoride.

Aspect 8. The method defined in any of the preceding aspects, wherein the amount of the fluorine-containing compound in the fluorine-containing solution provides a concentration of fluorine (F) in any range disclosed herein, for example, from about 0.01 to about 10 wt. %, from about 0.1 to about 10 wt. %, or from about 0.5 to about 5 wt. %, of fluorine (F) in the fluorine-containing solution.

Aspect 9. The method defined in any of the preceding aspects, wherein the fluorine-containing solution is substantially free of chlorine-containing compounds, for example, less than 100 ppmw.

Aspect 10. The method defined in any of the preceding aspects, wherein the fluorination step is conducted at a fluorination temperature in any fluorination temperature range disclosed herein, for example, from about 20° C. to about 95° C., from about 30° C. to about 80° C., or from about 20° C. to about 50° C.

Aspect 11. The method defined in any of the preceding aspects, wherein the fluorination step is conducted for a time period in any range of fluorination time periods disclosed herein, for example, from about 1 min to about 48 hours, from about 30 min to about 12 hours, or from about 1 to about 10 hours.

Aspect 12. The method defined in any of the preceding aspects, wherein the chlorine-containing stream comprises (or consists essentially of, or consists of) the chlorine-containing compound and any inert gas disclosed herein, for example, nitrogen.

Aspect 13. The method defined in any of the preceding aspects, wherein the chlorine-containing stream comprises (or consists essentially of, or consists of) chlorine gas ($Cl_2$) and nitrogen.

Aspect 14. The method defined in any of the preceding aspects, wherein the amount of the chlorine-containing compound in the chlorine-containing stream provides a concentration of chlorine (Cl) in any range disclosed herein, for example, less than about 10 vol. %, less than about 5 vol. %, in a range from about 0.05 to about 5 vol. %, or in a range from about 0.5 to about 3 vol. %, of chlorine (Cl) in the chlorine-containing stream.

Aspect 15. The method defined in any of the preceding aspects, wherein the chlorine-containing stream is substantially free of oxygen-containing compounds and/or fluorine-containing compounds, for example, less than 100 ppmw.

Aspect 16. The method defined in any of the preceding aspects, wherein the chlorination step is conducted at a chlorination temperature in any chlorination temperature range disclosed herein, for example, from about 20° C. to about 300° C., from about 30° C. to about 250° C., or from about 50° C. to about 200° C.

Aspect 17. The method defined in any of the preceding aspects, wherein the chlorination step is conducted for a time period in any range of chlorination time periods disclosed herein, for example, from about 1 to about 48 hours, from about 1 to about 12 hours, or from about 2 to about 8 hours.

Aspect 18. The method defined in any of the preceding aspects, wherein the decoking gas stream comprises (or consists essentially of, or consists of) any combination of an inert gas (one or more) and oxygen disclosed herein, for example, a mixture of nitrogen and oxygen, air, or a mixture of air and nitrogen.

Aspect 19. The method defined in any of the preceding aspects, wherein the decoking gas stream comprises a mole % of oxygen less than any maximum amount or in any range disclosed herein, for example, less than about 5 mole %, or in a range from about 0.5 to about 3 mole %.

Aspect 20. The method defined in any of the preceding aspects, wherein the decoking gas stream is substantially free of halogen-containing compounds (e.g., substantially halogen-free, substantially chlorine-free), for example, less than 100 ppmw.

Aspect 21. The method defined in any of the preceding aspects, wherein the decoking gas stream is substantially free of water, for example, less than 100 ppmw.

Aspect 22. The method defined in any of the preceding aspects, wherein the carbon burn step is conducted at a peak decoking temperature in any peak decoking temperature range disclosed herein, for example, from about 150° C. to about 600° C., from about 200° C. to about 500° C., or from about 300° C. to about 500° C.

Aspect 23. The method defined in any of the preceding aspects, wherein the carbon burn step is started at an initial decoking temperature which is the same as any chlorination temperature disclosed herein, for example, from about 20° C. to about 300° C., from about 30° C. to about 250° C., or from about 50° C. to about 200° C.

Aspect 24. The method defined in any of the preceding aspects, wherein the carbon burn step is conducted for a time period in any range of de-coking time periods disclosed herein, for example, from about 1 to about 72 hours, from about 12 to about 48 hours, or from about 1 to about 6 hours.

Aspect 25. The method defined in any of the preceding aspects, wherein the carbon burn step is conducted for a time period sufficient to reduce the wt. % of carbon on the chlorinated spent catalyst to less than any maximum weight percentage of carbon disclosed herein, for example, less than about 1 wt. %.

Aspect 26. The method defined in any of the preceding aspects, wherein the method further comprises a partial decoking step prior to the chlorination step, the partial decoking step comprising contacting the spent catalyst with a partial decoking gas stream comprising oxygen.

Aspect 27. The method defined in aspect 26, wherein the partial decoking gas stream comprises (or consists essentially of, or consists of) any combination of an inert gas (one or more) and oxygen disclosed herein, for example, a mixture of nitrogen and oxygen, or air.

Aspect 28. The method defined in any of aspects 26-27, wherein the partial decoking gas stream comprises a mole % of oxygen less than any maximum amount or in any range disclosed herein, for example, less than about 5 mole %, or in a range from about 0.5 to about 3 mole %.

Aspect 29. The method defined in any of aspects 26-28, wherein the partial decoking gas stream is substantially free of halogen-containing compounds (e.g., substantially halogen-free), for example, less than 100 ppmw.

Aspect 30. The method defined in any of aspects 26-29, wherein the partial decoking gas stream is substantially free of water, for example, less than 100 ppmw.

Aspect 31. The method defined in any of aspects 26-30, wherein the partial decoking step is conducted at a partial decoking temperature in any partial decoking temperature range disclosed herein, for example, from about 150° C. to about 250° C.

Aspect 32. The method defined in any of aspects 26-31, wherein the partial decoking step is conducted for a time period in any range of partial de-coking time periods disclosed herein, for example, from about 2 to about 24 hours.

Aspect 33. The method defined in any of aspects 26-32, wherein the partial decoking step is conducted for a time period sufficient to reduce the wt. % of carbon on the spent catalyst to any range of weight percentage of carbon disclosed herein, for example, from about 1 to 10 wt. %, or from about 0.5 to about 3 wt. %.

Aspect 34. The method defined in any of the preceding aspects, wherein the method further comprises a pre-drying step prior to the chlorination step, the pre-drying step comprising contacting the spent catalyst with a pre-drying gas stream comprising (or consisting essentially of, or consisting of) any inert gas disclosed herein, for example, nitrogen.

Aspect 35. The method defined in aspect 34, wherein the pre-drying gas stream is substantially free of oxygen-containing compounds, for example, less than 100 ppmw.

Aspect 36. The method defined in any of aspects 34-35, wherein the pre-drying step is conducted at a pre-drying temperature in any pre-drying temperature range disclosed herein, for example, from about 100° C. to about 500° C., from about 20° C. to about 400° C., or from about 180° C. to about 280° C.

Aspect 37. The method defined in any of aspects 34-36, wherein the pre-drying step is conducted for a time period in any range of pre-drying time periods disclosed herein, for example, from about 1 to about 48 hours.

Aspect 38. The method defined in any of aspects 34-37, wherein the pre-drying step is conducted for a time period sufficient to reduce the moisture content of the spent catalyst to less than any maximum moisture content of the spent catalyst disclosed herein, for example, less than about 4 wt. %, or less than about 1 wt. %.

Aspect 39. The method defined in any of the preceding aspects, wherein the method further comprises a chlorine purging step prior to the carbon burn step, the chlorine purging step comprising contacting the chlorinated spent catalyst with a chlorine purging stream comprising (or consisting essentially of, or consisting of) any inert gas disclosed herein, for example, nitrogen.

Aspect 40. The method defined in aspect 39, wherein the chlorine purging stream is substantially free of oxygen-containing compounds, for example, less than 100 ppmw.

Aspect 41. The method defined in any of aspects 39-40, wherein the chlorine purging stream is substantially free of halogen-containing compounds (substantially halogen-free), for example, less than 100 ppmw.

Aspect 42. The method defined in any of aspects 39-41, wherein the chlorine purging step is conducted at a chlorine purging temperature in any chlorine purging temperature range disclosed herein, for example, from about 20° C. to about 400° C., from about 30° C. to about 300° C., or from about 30° C. to about 250° C.

Aspect 43. The method defined in any of aspects 39-42, wherein the chlorine purging step is conducted for a time period in any range of chlorine purging time periods disclosed herein, for example, from about 1 to about 48 hours.

Aspect 44. The method defined in any of aspects 39-43, wherein the chlorine purging step is conducted for a time period sufficient to reduce the chlorine content of the outgoing chlorine purging effluent stream, after contacting the chlorinated spent catalyst, to less than any maximum chlorine content described herein, for example, less than about 100 ppmw of chlorine-containing compounds.

Aspect 45. The method defined in any of the preceding aspects, wherein the method further comprises an aging step after the fluorination step, the aging step comprising storing the fluorinated catalyst in the fluorine-containing solution at any suitable conditions, for example, a temperature from about 20° C. to about 100° C., a pressure from about ambient to about 500 psig, a time period of from about 1 minute to about 10 days, and under conditions in which the fluorinated catalyst is stationary or moving/mixing.

Aspect 46. The method defined in any of the preceding aspects, wherein the method further comprises a drying step after the fluorination step, the drying step comprising subjecting the fluorinated catalyst to conditions sufficient to reduce the solvent content of the fluorinated catalyst to less than any residual solvent content disclosed herein, for example, less than 15 wt. %, less than 12 wt. %, less than 10 wt. %, or less than 8 wt. % solvent, based on the weight of the catalyst.

Aspect 47. The method defined in aspect 46, wherein the conditions sufficient to reduce the solvent content comprise any suitable drying time, drying temperature, and drying pressure.

Aspect 48. The method defined in aspect 46, wherein the conditions sufficient to reduce the solvent content comprise a drying time in a range from about 1 to about 48 hr, or from about 2 to about 24 hr, a drying temperature in a range from about 15° C. to about 200° C., or from about 25° C. to about 150° C., and a drying pressure equal to atmospheric pressure or equal to any suitable sub-atmospheric pressure.

Aspect 49. The method defined in any of aspects 46-48, wherein the drying step comprises drying stationary fluorinated catalyst, fluidizing the fluorinated catalyst, or drying the fluorinated catalyst in a rotary dryer.

Aspect 50. The method defined in any of the preceding aspects, wherein the method further comprises a calcination step after the fluorination step, the calcination step comprising subjecting the fluorinated catalyst to any suitable calcination conditions.

Aspect 51. The method defined in aspect 50, wherein the calcination step is conducted at calcination conditions comprising a calcination temperature in any calcination temperature range disclosed herein, for example, from about 200° C. to about 800° C., from about 250° C. to about 600° C., or from about 300° C. to about 500° C.

Aspect 52. The method defined in any of aspects 50-52, wherein the calcination step is conducted at calcination conditions comprising a calcination time in any range of calcination time periods disclosed herein, for example, from about 30 min to about 48 hours, from about 1 hr to about 12 hr, or from about 2 hr to about 8 hr.

Aspect 53. The method defined in any of the preceding aspects, wherein the method further comprises an oxygen purging step after the carbon burn step, the oxygen purging step comprising contacting the de-coked catalyst with an oxygen purging stream comprising (or consisting essentially of, or consisting of) any inert gas disclosed herein, for example, nitrogen.

Aspect 54. The method defined in aspect 53, wherein the oxygen purging stream is substantially free of oxygen-containing compounds, for example, less than 100 ppmw.

Aspect 55. The method defined in any of aspects 53-54, wherein the oxygen purging stream is substantially free of halogen-containing compounds (substantially halogen-free), for example, less than 100 ppmw.

Aspect 56. The method defined in any of aspects 53-55, wherein the oxygen purging step is conducted at an oxygen purging temperature in any oxygen purging temperature range disclosed herein, for example, from about 25° C. to about 400° C., from about 30° C. to about 300° C., or from about 30° C. to about 250° C.

Aspect 57. The method defined in any of aspects 53-56, wherein the oxygen purging step is conducted for a time period in any range of oxygen purging time periods disclosed herein, for example, from about 1 to about 48 hours.

Aspect 58. The method defined in any of aspects 53-57, wherein the oxygen purging step is conducted for a time period sufficient to reduce the oxygen content of the outgoing oxygen purging effluent stream, after contacting the de-coked catalyst, to less than any maximum oxygen content described herein, for example, less than about 100 ppmw of oxygen-containing compounds.

Aspect 59. The method defined in any of the preceding aspects, wherein the method further comprises a reducing step after the fluorination step, the reducing step comprising contacting the fluorinated catalyst (or the calcined catalyst) with a reducing gas stream comprising (or consisting essentially of, or consisting of) molecular hydrogen.

Aspect 60. The method defined in aspect 59, wherein the reducing gas stream comprises a mole % of molecular hydrogen greater than any minimum amount or in any range disclosed herein, for example, greater than about 25 mole %, or greater than about 75 mole %.

Aspect 61. The method defined in any of aspects 59-60, wherein the reducing step is conducted at a peak reducing temperature in any peak reducing temperature range disclosed herein, for example, from about 400° C. to about 600° C.

Aspect 62. The method defined in any of aspects 59-61, wherein the reducing step is started at an initial reducing temperature that is the same as any drying temperature or any calcination temperature disclosed herein.

Aspect 63. The method defined in any of aspects 59-62, wherein the reducing step is conducted for a time period in any range of reducing step time periods disclosed herein, for example, from about 10 to about 30 hours.

Aspect 64. The method defined in any of the preceding aspects, wherein the catalyst support comprises a zeolite, an amorphous inorganic oxide, or any combination thereof.

Aspect 65. The method defined in any of the preceding aspects, wherein the catalyst support comprises an L-zeolite, a Y-zeolite, a mordenite, an omega zeolite, and/or a beta zeolite.

Aspect 66. The method defined in any of the preceding aspects, wherein the catalyst support comprises a potassium L-zeolite or a barium ion-exchanged L-zeolite.

Aspect 67. The method defined in any of the preceding aspects, wherein the catalyst support comprises a binder comprising alumina, silica, a mixed oxide thereof, or a mixture thereof.

Aspect 68. The method defined in any of the preceding aspects, wherein the transition metal comprises a Group 8-10 transition metal.

Aspect 69. The method defined in any of the preceding aspects, wherein the transition metal comprises platinum.

Aspect 70. The method defined in any of the preceding aspects, wherein the catalyst comprises any weight percentage range of transition metal disclosed herein, for example, from about 0.1 wt. % to about 10 wt. %, or from about 0.3 wt. % to about 5 wt. %, transition metal, based on the weight of the catalyst excluding carbon.

Aspect 71. The method defined in any of the preceding aspects, wherein the catalyst comprises any weight percentage range of platinum disclosed herein, for example, from about 0.1 wt. % to about 10 wt. %, or from about 0.5 wt. % to about 2 wt. %, platinum, based on the weight of the catalyst excluding carbon.

Aspect 72. The method defined in any of the preceding aspects, wherein the catalyst comprises platinum on a KL-zeolite.

Aspect 73. The method defined in any of the preceding aspects, wherein the catalyst further comprises chlorine and fluorine.

Aspect 74. The method defined in aspect 73, wherein the catalyst comprises any weight percentage range of chlorine and/or weight percentage range of fluorine disclosed herein, for example, from about 0.01 wt. % to about 5 wt. %, or from 0 to about 2 wt. % fluorine, and/or from about 0.01 wt. % to about 5 wt. %, or from 0 to about 2 wt. % chlorine, based on the weight of the catalyst excluding carbon.

Aspect 75. The method defined in any of aspects 73-74, wherein the catalyst comprises any molar ratio of chlorine:fluorine disclosed herein, for example, from about 0.3:1 to about 4:1.

Aspect 76. The method defined in any of the preceding aspects, wherein the chlorine-containing compound comprises hydrochloric acid, chlorine gas ($Cl_2$), carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethylammonium chloride, tetrapropylammonium chloride, tetrabutylammonium chloride, methyltriethylammonium chloride, or any combination thereof.

Aspect 77. The method defined in any of the preceding aspects, wherein the chlorine-containing compound comprises chlorine gas ($Cl_2$), carbon tetrachloride, or tetrachloroethylene.

Aspect 78. The method defined in any of the preceding aspects, wherein the fluorine-containing compound comprises hydrofluoric acid, 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethylammonium fluoride, tetrapropylammonium fluoride, tetrabutylammonium fluoride, methyltriethylammonium fluoride, or any combination thereof.

Aspect 79. The method defined in any of the preceding aspects, wherein the fluorine-containing compound comprises hydrofluoric acid, ammonium fluoride, tetramethylammonium fluoride, or a combination thereof.

Aspect 80. A reactivated catalyst or regenerated catalyst produced by the method defined in any of the preceding aspects.

Aspect 81. The catalyst defined in aspect 80, wherein the reactivated catalyst or regenerated catalyst has an activity in any range disclosed herein, for example, from about 70% to about 100% of the catalyst activity of a fresh reference catalyst of the same production run of catalyst, or substantially the same catalyst activity as that of the fresh reference catalyst, when tested on the same equipment, and under the same method and test conditions.

Aspect 82. The catalyst defined in any of aspects 80-81, wherein the reactivated catalyst or regenerated catalyst has a selectivity in any range disclosed herein, for example, from about 80% to about 105%, or from about 98% to about 105%, of the catalyst selectivity of a fresh reference catalyst of the same production run of catalyst, when tested on the same equipment, and under the same method and test conditions.

Aspect 83. The catalyst defined in any of aspects 80-82, wherein the reactivated catalyst or regenerated catalyst is characterized by an aromatics selectivity in any selectivity range disclosed herein, for example, from about 0.88 to about 0.94, or from about 0.90 to about 0.94.

We claim:

1. A method for regenerating a chlorinated spent catalyst comprising a transition metal and a catalyst support, the method comprising:
   (i) contacting the chlorinated spent catalyst with a decoking gas stream comprising oxygen to produce a de-coked chlorinated catalyst,
   wherein the chlorinated spent catalyst comprises from about 0.5 wt. % to about 3 wt. % of chlorine; and
   (ii) contacting the de-coked chlorinated catalyst with a fluorine-containing solution comprising a fluorine-containing compound in the liquid phase to produce a fluorinated catalyst; wherein:
   the transition metal comprises a Group 8-11 transition metal; and
   the catalyst support comprises a large pore zeolite having an average pore diameter in a range of from about 7 Å to about 12 Å.

2. The method of claim 1, wherein the chlorinated spent catalyst further comprises fluorine.

3. The method of claim 1, wherein the chlorinated spent catalyst comprises at least about 1 wt. % carbon.

4. The method of claim 1, wherein the de-coked chlorinated catalyst comprises less than about 0.5 wt. % carbon.

5. The method of claim 1, wherein:
   step (i) is conducted at a peak decoking temperature in a range from about 300° C. to about 500° C.;
   the decoking gas stream comprises an inert gas and oxygen; and
   the decoking gas stream is substantially free of halogen-containing compounds.

6. The method of claim 1, wherein an amount of the fluorine-containing compound in the fluorine-containing solution provides from about 0.1 to about 10 wt. % of fluorine (F) in the fluorine-containing solution.

7. The method of claim 1, wherein:
   step (ii) is conducted at a fluorination temperature in a range from about 20° C. to about 50° C.; and
   the fluorine-containing solution comprises water and at least one of ammonium fluoride and tetramethylammonium fluoride.

8. The method of claim 1, further comprising a drying step, a calcination step, or both a drying step and a calcination step, after step (ii).

9. The method of claim 1, wherein:
the transition metal comprises platinum; and
the catalyst support comprises a KL-zeolite and a binder comprising alumina, silica, a mixed oxide thereof, or a mixture thereof.

10. The method of claim 9, wherein:
the de-coked chlorinated catalyst comprises less than about 0.2 wt. % carbon; and
the fluorinated catalyst comprises from about 0.5 wt. % to about 3 wt. % of fluorine.

11. The method of claim 10, wherein the fluorinated catalyst comprises from about 0.3 wt. % to about 3 wt. % of platinum.

12. The method of claim 11, wherein:
the decoking gas stream comprises nitrogen and oxygen; and
the fluorine-containing solution comprises water and at least one of ammonium fluoride and tetramethylammonium fluoride.

13. A method for regenerating a de-coked chlorinated catalyst comprising a transition metal and a catalyst support, the method comprising:
contacting the de-coked chlorinated catalyst with a fluorine-containing solution comprising a fluorine-containing compound in the liquid phase to produce a fluorinated catalyst;
wherein:
the de-coked chlorinated catalyst comprises from about 0.5 wt. % to about 3 wt. % of chlorine;
the de-coked chlorinated catalyst comprises less than about 0.5 wt. % carbon;
the transition metal comprises a Group 8-11 transition metal; and
the catalyst support comprises a large pore zeolite having an average pore diameter in a range of from about 7 Å to about 12 Å.

14. The method of claim 13, wherein the de-coked chlorinated catalyst further comprises fluorine.

15. The method of claim 14, wherein the fluorinated catalyst comprises from about 0.5 wt. % to about 3 wt. % of fluorine.

16. The method of claim 13, wherein the de-coked chlorinated catalyst comprises less than about 0.2 wt. % carbon.

17. The method of claim 13, wherein an amount of the fluorine-containing compound in the fluorine-containing solution provides from about 0.1 to about 10 wt. % of fluorine (F) in the fluorine-containing solution.

18. The method of claim 13, wherein:
the de-coked chlorinated catalyst is contacted with the fluorine-containing solution at a fluorination temperature in a range from about 20° C. to about 50° C.; and
the fluorine-containing solution comprises water and at least one of ammonium fluoride and tetramethylammonium fluoride.

19. The method of claim 13, further comprising a step of drying the fluorinated catalyst, a step of calcining the fluorinated catalyst, or both drying and calcining the fluorinated catalyst.

20. The method of claim 13, wherein:
the transition metal comprises platinum; and
the catalyst support comprises a KL-zeolite and a binder comprising alumina, silica, a mixed oxide thereof, or a mixture thereof.

21. The method of claim 20, wherein:
the de-coked chlorinated catalyst comprises less than about 0.2 wt. % carbon;
the de-coked chlorinated catalyst further comprises fluorine;
the fluorinated catalyst comprises from about 0.5 wt. % to about 3 wt. % of fluorine; and
the fluorinated catalyst comprises from about 0.3 wt. % to about 3 wt. % of platinum.

* * * * *